US010221193B2

(12) United States Patent
Johnstone et al.

(10) Patent No.: US 10,221,193 B2
(45) Date of Patent: Mar. 5, 2019

(54) PHOTOINITIATED REACTIONS

(75) Inventors: Robert A. W. Johnstone, Bebington (GB); Rui Manuel da Silva Loureiro, Lisbon (PT)

(73) Assignee: Lintfiled Limited, Green Tonbridge, Kent (GB)

( * ) Notice: Subject to any disclaimer, the term of this patent is extended or adjusted under 35 U.S.C. 154(b) by 1588 days.

(21) Appl. No.: 13/522,812

(22) PCT Filed: Jan. 17, 2011

(86) PCT No.: PCT/GB2011/050064
§ 371 (c)(1),
(2), (4) Date: Jan. 16, 2013

(87) PCT Pub. No.: WO2011/086389
PCT Pub. Date: Jul. 21, 2011

(65) Prior Publication Data
US 2013/0105297 A1    May 2, 2013

(30) Foreign Application Priority Data

Jan. 18, 2010  (GB) .................................. 1000752.4

(51) Int. Cl.
C08F 2/50        (2006.01)
B01J 19/12       (2006.01)
C07D 495/10      (2006.01)

(52) U.S. Cl.
CPC .......... C07D 495/10 (2013.01); B01J 19/123 (2013.01); C08F 2/50 (2013.01)

(58) Field of Classification Search
CPC ......... C07D 495/10; C08F 2/50; B01J 19/123
(Continued)

(56) References Cited

U.S. PATENT DOCUMENTS 4,026,705 A   5/1977 Crivello
4,072,694 A   2/1978 Brattesani
(Continued)

FOREIGN PATENT DOCUMENTS

EP   0874282 B1   12/2003
EP   1307783 B1   10/2006
(Continued)

OTHER PUBLICATIONS

Cepeda, et al.; Catalyzed Oxidation Kinetics of Anthracene with Oxygen in Ethylene Glycol; Industrial & Engineering Chemistry Research, vol. 26, No. 12, 1987, (Cepeda, Emilio A.; Diaz, Mario), pp. 2401-2403, ISSN: 0888-5885.
(Continued)

*Primary Examiner* — Nicholas A Smith
*Assistant Examiner* — Colleen M Raphael
(74) *Attorney, Agent, or Firm* — Merchant & Gould PC

(57) ABSTRACT

Disclosed is a method for the photoinitiated transformation of a transformable reactive substrate. The method includes an initial step in which a protected ketone photoinitiator species which is present in the substrate is deprotected to form the corresponding ketone photoinitiator species for use in a subsequent photoinitiated reaction in the method. The ketone group of the photoinitiator is protected by an unsubstituted 1, 3 dioxolane group. Also disclosed are a composition which may be used in the method, the use of the protected ketone photoinitiator in a photoinitiated reaction, as well as the protected ketone photoinitiators themselves.

23 Claims, 9 Drawing Sheets

(58) Field of Classification Search
USPC .......................................... 204/157.6–158.21
See application file for complete search history.

(56) References Cited

U.S. PATENT DOCUMENTS

| | | | |
|---|---|---|---|
| 4,188,224 | A | 2/1980 | Felder |
| 4,795,766 | A | 1/1989 | Rutsch |
| 4,923,941 | A | 5/1990 | Bailey |
| 5,346,804 | A * | 9/1994 | Pawlowski ............ C07C 309/65 430/176 |
| 5,506,089 | A * | 4/1996 | Gybin et al. ...................... 522/6 |
| 5,510,539 | A | 4/1996 | Berner |
| 5,998,495 | A | 12/1999 | Oxman |
| 6,057,078 | A | 5/2000 | Cunningham |
| 6,087,062 | A * | 7/2000 | Cunningham et al. ........... 522/7 |
| 6,197,842 | B1 | 3/2001 | Marchin |
| 6,335,143 | B1 | 1/2002 | Sumino |
| 6,388,104 | B1 | 5/2002 | Hartl |
| 6,479,039 | B1 | 11/2002 | Dyer |
| 6,482,565 | B1 * | 11/2002 | Jung et al. ................. 430/270.1 |
| 6,770,420 | B2 * | 8/2004 | Dietliker et al. .......... 430/270.1 |
| 6,844,375 | B2 | 1/2005 | Hartl |
| 7,425,585 | B2 | 9/2008 | Kura |
| 7,585,611 | B2 | 9/2009 | Kato |
| 7,943,650 | B2 * | 5/2011 | Gupta et al. ................... 514/399 |
| 2004/0014833 | A1 * | 1/2004 | Bradley ............................ 522/6 |
| 2006/0159856 | A1 * | 7/2006 | Kunz et al. .................... 427/402 |
| 2007/0163705 | A1 | 7/2007 | Dollase et al. |
| 2007/0185225 | A1 | 8/2007 | Bradley |
| 2007/0275962 | A1 * | 11/2007 | Koul .................... C07D 209/42 514/233.8 |

FOREIGN PATENT DOCUMENTS

| | | |
|---|---|---|
| EP | 1487888 | 10/2008 |
| EP | 1772774 B1 | 6/2012 |
| EP | 0887706 A1 | 12/2012 |
| GB | 1425498 A | 2/1976 |
| GB | 1575873 A | 10/1980 |
| JP | H04-104157 A | 4/1992 |
| JP | 62-25179 A | 8/1994 |
| JP | 08-053373 A | 2/1996 |
| JP | 8305019 A | 11/1996 |
| JP | 09-179299 A | 7/1997 |
| JP | 09-325209 A | 12/1997 |
| JP | 11-269235 A | 10/1999 |
| JP | 11-270248 A | 10/1999 |
| JP | 2000105945 A | 4/2000 |
| WO | WO 2002/012350 A2 | 2/2002 |

OTHER PUBLICATIONS

Crivello et al: Photoinitiators for Free Radical Cationic & Anionic Photopolymerisation 2nd Edition; SITA Technology Ltd., 1998; 9 pages.

Davidson R S et al: "The photoinitiated polymerization of 4-methylene-1,3-dioxolanes" Journal of Photochemistry and Photobiology, A: Chemistry., vol. 100, 1997, pp. 185-193, XPOO2200649.

Hiraguri Y et al: "Novel Synthesis of a Polyketone via Radical Ring-Opening Polymerization of 2,2-Diphenyl-4-methylene-1,3-dioxolane" Journal of the American Chemical Society, vol. 109, 1987, pp. 3779-3780, XP002200650.

Jackson, et al.; Benzocyclobutenedione Monoketal. A 1,4-Dipole Equivalent for Anthracyclinone Synthesis. Synthesis of (+)-4-Demethoxydaunomycinone; Journal of the American Chemical Society; 1979; vol. 101, No. 14, pp. 3989-3990, ISSN: 0002-7863.

LiBassi et al; Photoinitiators for the Simultaneous Generation of Free Radicals and Acid Hardening Catalysts; Radcure 1986 Proceedings, Dec. 1987; 17 pages.

Mitchell, et al: "A New High-Speed Photopolymerization System," Journal of Imaging Science, vol. 30 (5), Sep./Oct. 1988, pp. 215-217.

Reese et al; Xanthen-9-ylidene protecting groups in glycerol chemistry; J. Chem. Soc., Perkin Trans. 1, 2001, 1807-1815.

Reese, et al; Xanthen-9-ylidene and 2,7-dimethylxanthen-9-ylidene protecting groups; Tetrahedron Lett., 2001, 42, 1789-1791.

Shirai, et al: Photoacid and Photobase Generators: Chemistry and Applications to Polymeric Materials, Prog. Poly. Sci, 1996, vol. 21, 1-18.

Spangler, et al; mechanistic Aspects of the Annelation Reactions of Benzocylobutenedione Monoketals with Vinyllithium Reagents; Journal of Organic Chemistry, 1984; vol. 49, No. 10, 1984; pp. 1800-1806, ISSN: 0022-3263.

Swenton, et al; 1,4-Dipole-Metalated Quinone Strategy to (+)-4Demethoxydaunomycinone and (+)-Daunomycinone. Annelation of Benzocyclobutenedione Monoketals with Lithioquinone Bisketals; Journal of Organic Chemistry; 1981, vol. 46, No. 24, pp. 4825-4836, ISSN: 0022-3263.

Taskinen E., et al; Relative Thermodynamic Stabilities of 2-Substituted 4-Methylene-1,3-dioxolanes and 4-Methyl-1,3-dioxoles; Structural Chemistry, 1997; vol. 8 No. 6.

Bradley et al, Journal of Photochemistry and Photobiology A: chemistry 100 (1996) 109-118.

International Preliminary Report on Patentability, PCT/GB2011/050064, dated Jul. 24, 2012.

International Search Report, PCT/GB2011/050064, dated Mar. 23, 2011.

Search Report, UK Patent Application GB000752.4, dated Aug. 5, 2010.

International Search Report & Written Opinion from PCT/GB2011/050064, dated Mar. 23, 2011.

Huet et al., Jan. 1978, "Wet Silica Gel; A Convenient Reagent for Deacetalization", Synthesis 1978, Georg Thieme Publishers, pp. 63-65.

JP Office Action dated Aug. 15, 2017 issued in corresponding JP Appln. No. 2016-128661.

English translation of JP Office Action dated Aug. 15, 2017 issued in corresponding JP Appln. No. 2016-128661.

English Translation of JP Patent H04104157.

* cited by examiner

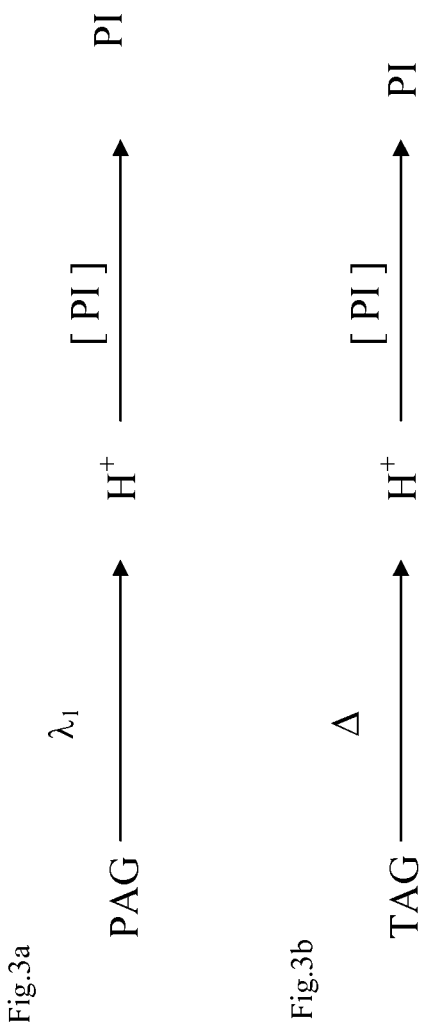

PHOTOINITIATED REACTIONS

RELATED APPLICATIONS

This application is a 35 U.S.C. § 371 filing of International Application No. PCT/GB2011/050064 filed Jan. 17, 2011, which claims priority to United Kingdom Patent Application No. 1000752.4 filed Jan. 18, 2010. The entire contents of each of the above documents are incorporated herein by reference.

This invention relates to photoinitiated reactions, for example curing and polymerisation reactions carried out under irradiation by electromagnetic radiation. More particularly it relates to UV curing as used in photopolymer technology, as well as photoinitiated colour forming reactions.

BACKGROUND

Within the growing realm of UV curing technology, one of the most important applications is in photo-imaging. Ever since the birth of photography, new and innovative ways of obtaining images by exposure to light have been explored; even the silver halide process itself, which still forms the core of non-digital photography, has undergone substantial change, as for example when the introduction of T-grain emulsions took place.

Although substantial improvements in photopolymer technology have been made over the last 20 years, the sensitivity of the processes is still very limited compared with the photosensitivity of the silver halide process. One of the major goals in photopolymer science is to approach the sensitivity of silver halide based processes.

Two basic methods of increasing the photopolymer quantum yield beyond unity exist. The first of these is most familiar as the acrylate chemistry used in most commercial free radical UV cure systems. The approach here is that of the chain reaction in which one or more photoinitiators that are exposed to electromagnetic radiation of a suitable wavelength/energy, absorb photons incident upon them. The energy of the photon is used chemically by the photoinitiators to generate free radicals in the irradiated substrate, each of which is then capable of causing many polymerisable molecules to polymerise very quickly resulting in a high quantum yield of polymerisation. Thus the quantum yield for this process is high but still not as high as that overall for silver halide photography.

The second fundamental form of photopolymer quantum yield enhancement is exemplified by the cationic UV curing systems. In this instance, the absorbed photon generates a catalytic monomer species which is capable of catalysing polymerisation, cross-linking, or even molecular cleavage. This technology has been described as capable of producing "living polymers" which will continue growing as long as substrate monomer molecules are still available. The reactions are, however, relatively slow compared with the chain reactions of the free radical process. Furthermore, although the quantum yield in terms of reacted molecules is theoretically near infinite, the slow reactions limit spatial resolution by reason of diffusion of active species out of the imaged area.

A limitation in terms of photopolymer imaging has always been the amount of time needed to deliver an adequate amount of energy to the area to be imaged. The delivery of a large amount of energy is easy. High intensity sources of radiation, simple reflectors and conveyor belts used in combination enable this aim to be achieved. For imaging, the radiation needs to be collimated and delivered in a controlled fashion. To collimate the output from any lamp involves a substantial loss of intensity. The subsequent use of optical components and even phototools serves to reduce the energy from even a very powerful source to a remarkably low level.

It is within this environment that the usage of lasers for imaging has developed. Although the radiant flux that such lasers will deliver is relatively low, the intrinsic collimation and the intensity of photons delivered at a given wavelength, make the laser a useful light source. Computer guided beam manipulation in combination with mirrors enables one to eliminate photo tool usage, and further enhances the number of photons available for the photochemistry. Nevertheless, these improvements have been only incremental, and laser imaged photopolymer processes are still slow.

In the silver halide process, the actual efficiency of the photochemistry is relatively low compared with chain reaction processes. Each photon produces only a single silver atom, thus the quantum efficiency is only one (or, in practice, less than one). The overall sensitivity of the silver process to light only becomes obvious by virtue of the development step when many more silver atoms are produced. Wherever a silver atom has been produced by irradiation with light, the silver available accelerates the development reaction, via an autocatalytic reaction, which in turn produces more silver. Thus the quantum efficiency of "image formation" can be varied from one to infinity, owing to the propagation that occurs in this second stage. However, the propagation occurs only within a grain boundary, viz. the silver atom produced in one grain can be completely developed but adjacent grains are not developed. Resolution of image details is, therefore, limited by grain size in the silver halide process.

Bradley et al Journal of Photochemistry and Photobiology A: chemistry 100 (1996) 109-118 describes the development of vinyl dioxolane based monomers as a more amenable alternative to vinyl ethers conventionally used as monomers for cationic UV curing. Such a material is (2,2'-diphenyl-4-methylene-1,3-dioxolane).

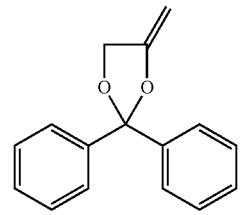 [SMILES: C=C1COC(c2ccccc2)(c2ccccc2)O1]

EP-A-1307783 describes a process in which a protected (also referred to as "blocked" or "latent") photoinitiator is included in a reactive substrate. The protected photoinitiator is deprotected in situ and is available for a subsequent photoinitiated reaction. The protected photoinitiator is a protected ketone photoinitiator in which the ketone group is protected by a methylene 1, 3 dioxolane group.

It has been found that the prior art ketone photoinitiators having a methylene-1,3-dioxolane moiety are not completely stable and decompose at room temperature or in the presence of light or very small quantities of even quite weak acid. The manufacture, handling and storage of photoinitiators based on such materials in commercial quantities may thus be difficult. A need exists for a more stable material which would still function as a blocked initiator under the correct conditions.

SUMMARY OF THE INVENTION

It has now unexpectedly been found that the stability problems of the protected photoinitiators of EP-1307783 can be overcome by the use of an unsubstituted 1, 3 dioxolane protecting group on the ketone photoinitiator. Ketone photoinitiators protected with an unsubstituted 1, 3 dioxolane group have been found to be stable in the presence of weak acids and light, but to rapidly deprotect in the presence of strong acid. Such advantageous properties were not found in respect of other dioxolane protecting groups tested, in particular where the protecting group was 4-chloromethyl dioxolane or 4-methyl dioxolane. For such protecting groups, the unblocking by deketalization proceeds too slowly to be effective.

Thus, in accordance with one aspect of the present invention, there is provided a method for the photoinitiated transformation of a transformable reactive substrate, for example a substrate which comprises polymerisable constituents, and/or cross-linkable constituents and/or colour-changeable constituents. In the method, a protected ketone photoinitiator species is included in the substrate, and the method includes a step in which the protected ketone photoinitiator is deprotected in situ to form the corresponding ketone photoinitiator species for use in a subsequent photo reaction or photoinitiated reaction in the method. As noted above, in the present invention, the ketone group of the photoinitiator is protected by an unsubstituted 1, 3 dioxolane group.

In accordance with another aspect of the invention, there is provided a method for the photoinitiated transformation of a transformable reactive substrate (for example the polymerisation of a polymerisable substrate and/or the cross-linking of a cross-linkable substrate and/or the colour change of a colour-changeable substrate), said method comprising:

(a) applying to the surface of a support a coating which comprises the reactive substrate, a protected ketone photoinitiator and one or more species capable of forming acid in response to an external stimulus, wherein the ketone group of the photoinitiator is protected by an unsubstituted 1,3 dioxolane group, and wherein the ketone photoinitiator, when deprotected by said acid, is capable of forming a reactive species on exposure to electromagnetic radiation of a suitable wavelength or energy;

(b) applying an external stimulus to said coating to form acid where the external stimulus is applied, whereby said acid reacts with and causes deprotection of the protected ketone photoinitiator, and wherein the external stimulus is not effective to generate reactive species from the deprotected ketone photoinitiator; and (c) exposing the coating to electromagnetic radiation of a suitable wavelength or energy to generate a reactive species from the ketone photoinitiator which, directly or indirectly, is capable of initiating transformation of the transformable reactive substrate in said regions.

In this aspect of the invention, the protected ketone photoinitiator and/or the species capable of generating acid may be included in a coating composition with the reactive substrate for application to the surface. Alternatively, the coating may be applied in more than one step in which first the reactive substrate is applied to the surface, optionally with one or other of the other components, followed by a subsequent step or steps in which the other component or components are supplied to form the coating on the surface.

In accordance with a further aspect of the invention, there is provided a method for the photoinitiated transformation of a transformable reactive substrate (for example the polymerisation of a polymerisable substrate and/or the cross-linking of a cross-linkable substrate and/or the colour change of a colour-changeable substrate), said method comprising:

(a) applying to the surface of a support a coating which comprises the reactive substrate and a protected ketone photoinitiator, wherein the ketone group of the photoinitiator is protected by an unsubstituted 1,3 dioxolane group, and wherein the ketone photoinitiator, when deprotected by acid, is capable of forming a reactive species on exposure to electromagnetic radiation of a suitable wavelength or energy;

(b) applying an acid to said coating to cause deprotection of the protected ketone photoinitiator; and (c) exposing the coating to electromagnetic radiation of a suitable wavelength or energy to generate a reactive species from the ketone photoinitiator which, directly or indirectly, is capable of initiating transformation of the transformable reactive substrate in said regions.

In accordance with another aspect of the invention, there is provided the use, in a photoinitiated reaction, of a protected ketone photoinitiator, wherein the ketone group of the photoinitiator is protected by an unsubstituted 1, 3 dioxolane group.

In a yet further aspect of the invention, there is provided a composition which comprises a transformable reactive substrate, a protected ketone photoinitiator wherein the ketone group of the photoinitiator is protected by an unsubstituted 1, 3 dioxolane group, and optionally a species capable of generating acid. The composition may also include optionally, various organic and/or inorganic pigments and filler materials, flow and levelling agents, solvents, diluents, drying/curing agents, cure accelerators, inhibitors, pH buffering agents, plasticisers, chain transfer agents.

The invention further provides a ketone photoinitiator in which the ketone moiety is protected by a 1, 3 dioxolane group. The protected ketone photoinitiator may have the formula (I):

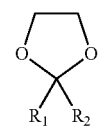

wherein $R_1$ is phenyl or substituted phenyl;
$R_2$ is phenyl, substituted phenyl or substituted alkyl;
and wherein, when each of $R_1$ and $R_2$ is phenyl or substituted phenyl, the respective phenyl groups may optionally be linked by a bridging moiety to form a structure having the following framework:

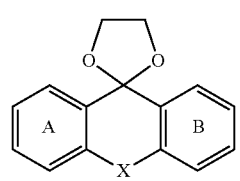

where X is S or >C=O and where each of the A and B rings may be substituted;

or wherein $R_1$ and $R_2$ may be joined to form a conjugated ring system which is optionally substituted.

BRIEF DESCRIPTION OF THE DRAWINGS

FIGS. 3a and 3b illustrate embodiments in which acid is generated by a photo acid generator or a thermal acid generator, and the acid then functions to deprotect the protected photoinitiator.

DETAILED DESCRIPTION OF THE INVENTION

Figure 1:
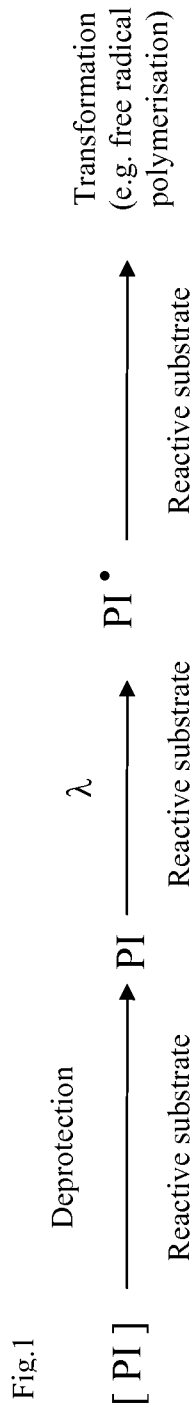
FIG. 1 illustrates an embodiment in which a protected photoinitiator is deprotected and the photoinitiator is subsequently involved in a photoinitiated reaction.

As described above, the present invention provides for the use of a protected ketone photoinitiator, in which the ketone moiety is protected by an unsubstituted 1, 3 dioxolane group, in photoinitiated reactions, such as those already described in EP-A-1307783. An advantage of the use of the protected ketone photoinitiator of the invention compared to the protected photoinitiator used in the prior art reference, (in which the ketone group is protected by a methylene 1, 3 dioxolane group) is that the protected photoinitiator used in the present invention is stable at room temperature and in the presence of light or very small quantities of weak acid, which facilitates manufacture and commercial use. The protecting group is however easily removable under conditions of strong acid.

As reported in EP-A-1307783, the acid-catalysed photopolymerization using a cationic species and the 2,2'-diphenyl-4-methylene-1,3-dioxolane species does not proceed via a simple cationic polymerisation but rather occurs rapidly via a ROMP-like (Ring Opening Metathesis Polymerisation) process in which a ketone is produced that is to act as photoinitiator in the second photoreaction.

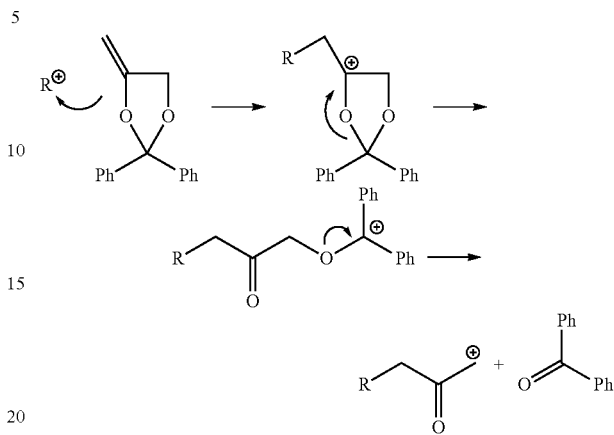

In the present invention, the methylene group is absent and this reaction is not possible. It was therefore expected that the deketalisation reaction to unblock the protected photoinitiator would proceed slowly. Indeed, slow unblocking was found where the protecting group was a 4-chloromethyl dioxolane or 4-methyl dioxolane group. Instead, and unexpectedly, where the protecting group was an unsubstituted dioxolane group, the reaction was found to be fast in the presence of strong acids but did not occur in the presence of weak acids or light.

Without wishing to be bound by theory, the following mechanism is postulated.

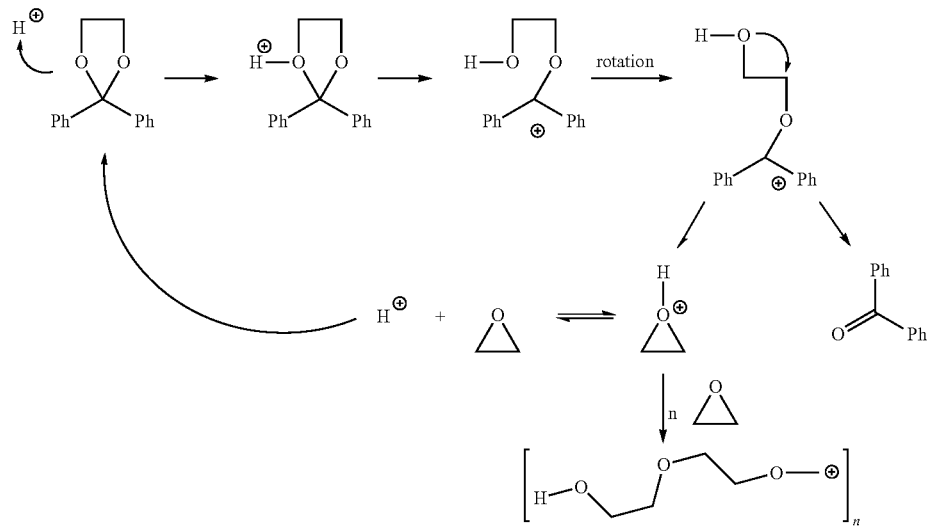

Under anhydrous conditions, the dioxolane protected photoinitiator cannot decompose by formation of a diol and regeneration of the parent initiator and must decompose through a different mechanism. This new mechanism, shown above, is very different from the mechanism by which 2,2'-diphenyl-4-methylene-1,3-dioxolane decomposes under acidic conditions as described by Bradley et al and in EP-A-1307783.

Protonation of the methylene group on the dioxolane ring, which triggers its decomposition, is not possible because there is no methylene group in the unsubstituted dioxolane.

In the absence of any cation-quenching materials, the simple dioxolane behaves as a ketal protected carbonyl compound and the process generates a polyether as the dioxolane ring is opened, generating the theoretical parent ketone for the dioxolane ring. The most obvious decomposition mode is for the dioxolane to form epoxyethane after protonation of one of the oxygens of the dioxolane ring. The dioxolane ring opening reaction proceeds with formation of a second strained ring structure (an epoxide), which reacts further to cause ring opening, producing the polyether and more of the ketone that is to act as a photoinitiator in a second photoreaction and giving back the proton, making the reaction self catalytic as shown above.

Evidence to support this theory has been demonstrated by analytical methods using 2-isopropylthioxanthone (ITX), a well known initiator of photochemical induced acrylate polymerisation, which has been blocked using the unsubstituted dioxolane to form the protected (or latent) photoinitiator (DITX). The following findings were made.

(1) When DITX is subjected to chemical ionization mass spectrometry (anhydrous vapour phase which normally gives very stable protonated molecular ions), the expected molecular ion is almost non-existent but there is mostly decomposition by loss of an epoxyethane molecule to give protonated ITX.

(2) NMR spectra from experiments with DITX, show that epoxyethane forms a polymer (polyoxyethylene) and nothing else, other than ITX indicating that the reason for the higher than expected reactivity of DITX to acid lies in the mechanism of epoxide formation shown above.

Unlike the 2,2'-diphenyl-4-methylene-1,3-dioxolane in the prior art, it has been found that free radical polymerisation does not occur.

In accordance with the present invention, the protected ketone photoinitiator is included in a transformable reactive substrate comprising constituents which are capable of transformation in a photo reaction or a photoinitiated reaction. For example the reactive substrate may be a substrate which comprises polymerisable constituents, and/or a substrate which comprises cross-linkable constituents and/or a substrate which comprises colour-changeable constituents. An example of a suitable substrate is a mixture of acrylate resins and/or monomers.

The reactive substrate may be applied as a coating to the surface of a support.

The constituents of the reactive substrate are caused to be transformed in a method which includes a step in which the protected ketone photoinitiator is deprotected in situ to form the corresponding ketone photoinitiator species for use in a subsequent photo reaction or photoinitiated reaction in the method.

In an embodiment, the subsequent photoinitiated reaction may involve exposing the reactive substrate with the deprotected ketone photoinitiator therein to photoreaction conditions wherein electromagnetic radiation of a suitable wavelength/energy causes the transformable constituents (eg polymerisable and/or cross-linkable constituents and/or colour-changeable constituents) in the substrate to undergo transformation (eg polymerisation and/or cross-linking and/or colour change). In this step, the radiation, for example actinic radiation (such as UV radiation), may be applied as a flood irradiation.

The exposure of the reactive substrate with the deprotected ketone photoinitiator therein to suitable photoreaction conditions typically causes the photoinitiator to form a reactive species, such as a free radical, but which alternatively may be an excited state of the molecule. This reactive species then directly or indirectly causes the transformable constituents (eg polymerisable and/or cross-linkable constituents and/or colour changeable constituents) in the substrate to undergo transformation (eg polymerisation and/or cross-linking and/or colour change).

For example, in some embodiments, the photoreaction conditions may directly lead to formation of free radical species (unimolecular bond cleavage), or may indirectly lead to formation of free radical species by interaction with a coinitiator species or synergist present in the reactive substrate (see FIG. 1).

Typically, in embodiments where the photoreaction conditions cause the formation or generation of a free radical species from the ketone photoinitiator, this free radical species will directly initiate transformation of the transformable constituents in the reactive substrate. Thus, for example, the transformation may be a free radical promoted polymerisation.

In other embodiments the deprotected ketone photoinitiator may function as a sensitiser, in which case it is employed in conjunction with a suitable second photoinitiator or synergist species which is included in the reactive composition. In these embodiments, photoreaction conditions cause the ketone photoinitiator to be promoted to an excited state. This reactive species interacts with the second photoinitiator or synergist, for example by transferring its energy to the other species, which initiates (directly or indirectly) transformation of the transformable constituents in the reactive substrate. In such embodiments, where the ketone photoinitiator functions as a sensitiser, it may return to its ground state after interaction and so be available for further excitation under suitable photoreaction conditions.

Figure 2A:
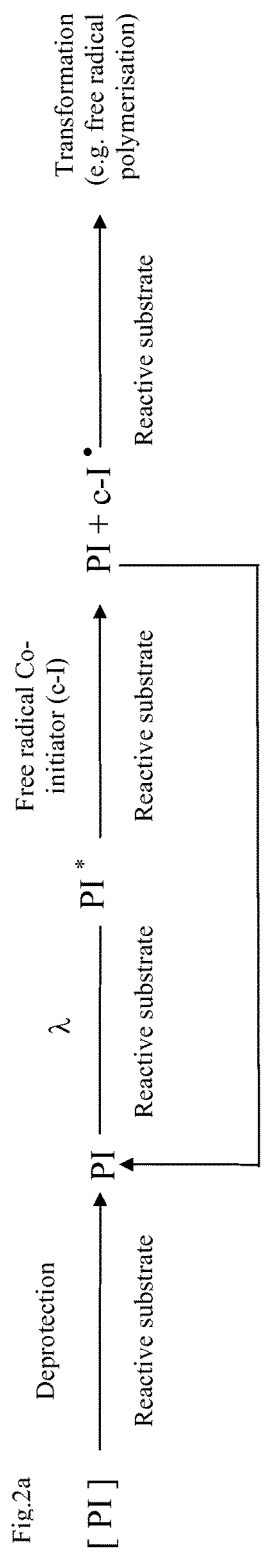
FIG. 2a-2c illustrate embodiments in which the photoinitiator functions as a sensitiser.
Figure 2B:
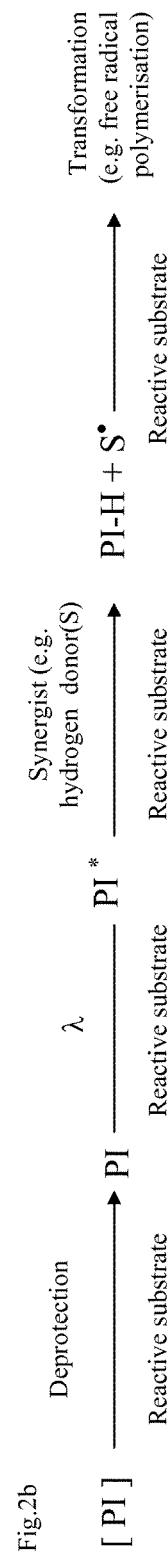
Figure 2C:
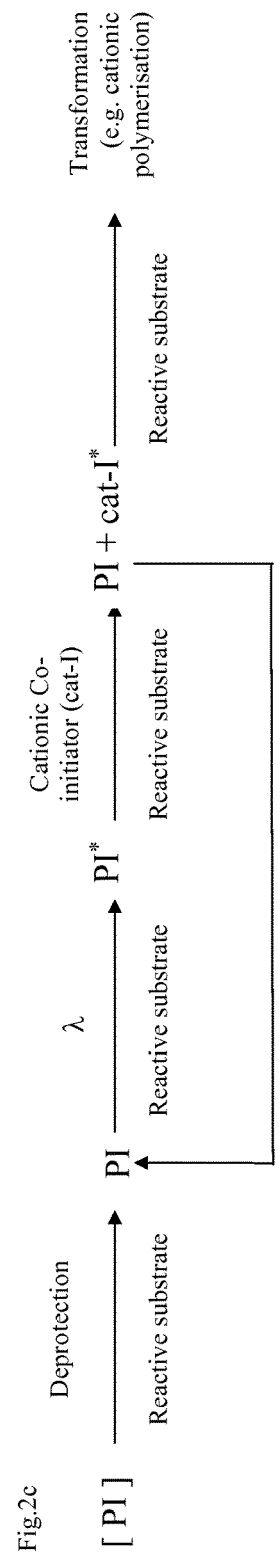

In these embodiments where the ketone photoinitiator functions as a sensitiser, the second photoinitiator may be a radical photoinitiator or a cationic photoinitiator (see FIGS. 2a, 2b ad 2c).

As noted above, the protected ketone photoinitiator is deprotected in situ, in what may be regarded as a first stage of the method of the invention, and the deprotected ketone photoinitiator is then used in a subsequent photoinitiated reaction.

Deprotection may be accomplished by including in the reactive substrate a species which is capable of generating acid in response to an external stimulus, the acid being effective for deprotecting the protected photoinitiator. This external stimulus may be exposure to electromagnetic radiation of a suitable wavelength or energy which is effective to cause generation of acid from the acid-generating species (see FIG. 3a, where "PAG" stands for photo acid generator). However, in principle other external stimuli may be employed, such as the application of thermal energy to cause generation of acid from a species which is thermally decomposable to yield an acid catalyst for the deprotection of the protected photoinitiator. An example of such a species is a blocked p-toluene sulphonic acid (see FIG. 3b where "TAG" stands for thermal acid generator).

For example, the unsubstituted 1,3-dioxolane group on the protected photoinitiator may for example be removed in a photoreaction which takes place under initial photoreaction conditions, which may involve a low energy dosage of radiation, for example actinic radiation (FIG. 3a). The protected ketone photoinitiator may be deprotected throughout the entirety of the reactive substrate or throughout only portions of the reactive substrate. To achieve deprotection throughout only portions of the substrate, this radiation may for example be applied imagewise by a laser or through a suitable phototool (FIG. 3b, λ₁ applied imagewise.

Where the substrate is applied as a coating on a support, the protected ketone photoinitiator may be deprotected throughout the entire of the support or throughout only portions of the support.

Alternatively, deprotection may be achieved by applying an acid, capable of causing deprotection to occur directly, or an acid generating species which is capable of generating acid in response to an external stimulus, onto a surface of the reactive substrate in a separate step, such as by spraying or ink jet printing.

The acid applied directly to the substrate or generated by the acid generating species, which is included in or subsequently applied to the substrate, is suitable to effect deprotection of the protected ketone photoinitiator. In this connection, the acid-generating species should be one which is capable of generating an acid, or the acid itself should be, of a suitable strength to deprotect the deprotected ketone photoinitiator. If necessary, appropriate tests can be carried out to match an acid-generating species to the specific ketone photoinitiator selected.

Figure 4:
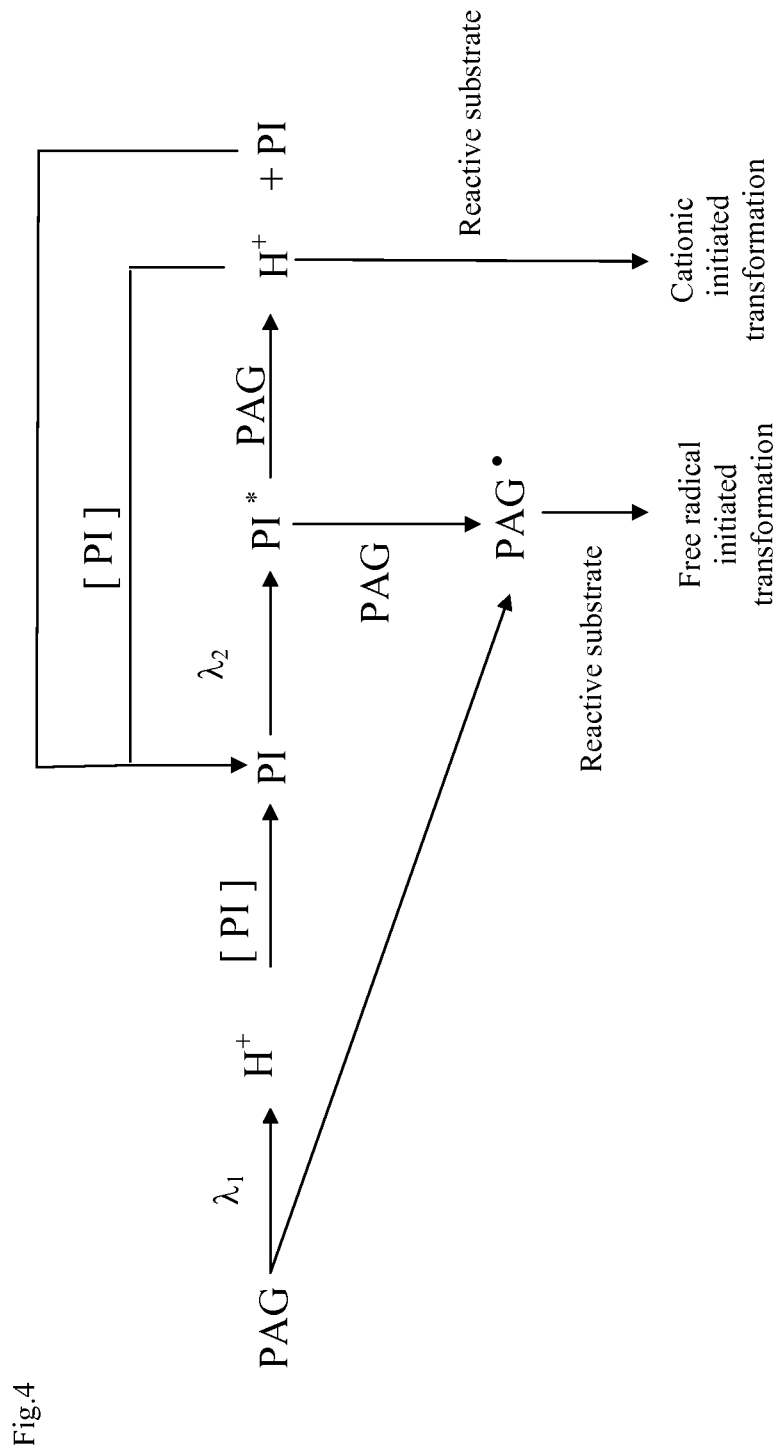
FIG. 4 illustrates an embodiment in which an acid generator and protected photoinitiator function in an auto-accelerative manner.

In some embodiments, the acid-generating species may also play a role as co-initiator in the subsequent photoinitiated reaction involving the deprotected ketone photoinitiator, where, in the subsequent stage, the exposure to electromagnetic radiation of a suitable wavelength causes the formation of a reactive species which interacts with this co-initiator to generate free radicals, capable of initiating transformation under suitable conditions of the transformable constituents in the reactive substrate, and/or of further acid capable of initiating transformation, under cationic conditions, of the transformable constituents in the reactive substrate and/or causing further deprotection of the protected ketone in an auto-accelerative fashion (see FIG. 4). This embodiment is discussed further below.

As previously mentioned, deprotection of the ketone photoinitiator may be accomplished in an imagewise fashion, for example, using a photomask or laser, that is to say the ketone photoinitiator is deprotected in selected regions of the surface of the support. This may be effected by exposure of the selected regions of the reactive substrate to electromagnetic radiation of a suitable wavelength to effect deprotection, as previously discussed. The result is that the ketone photoinitiator is only deprotected in the selected regions. This step may be conducted at relatively low energy. Alternatively, selective deprotection may be achieved by applying an acid and/or acid generating species to the surface of the substrate in a separate imagewise step, such as by ink jet printing, so that the acid, and/or the acid generated by the acid generating species in response to exposure to a suitable external stimulus, causes deprotection to occur in areas corresponding to the areas to which the acid and/or acid generating species have been applied. In the subsequent stage, exposure to electromagnetic radiation of a suitable wavelength which is different to the wavelength of the electromagnetic radiation used in the initial step where deprotection was carried out photochemically, and is matched to the ketone photoinitiator will lead to transformation of the transformable constituents in the reactive substrate only in the selected regions. Exposure to electromagnetic radiation in this step may be high energy to accomplish rapid curing.

In an alternative approach, the protected ketone photoinitiator may be deprotected in the first stage over the entire surface of the support. Subsequent exposure to electromagnetic radiation of a suitable wavelength matched to the ketone photoinitiator is then carried out imagewise in selected regions of the surface of the support, for example using a photomask or laser. This alternative approach allows, for example, a preliminary step to be carried out in which the reactive substrate is prepared under conditions (for example radiation such as may be used in drying) which might otherwise be effective to activate the ketone photoinitiator, if deprotected. However, because the ketone photoinitiator is protected at this stage, it is not available to be activated and so any substantial undesired transformation of the transformable constituents in the reactive substrate is avoided.

The present invention also relates to a ketone photoinitiator in which the ketone moiety is protected by a 1, 3 dioxolane group. The protected ketone photoinitiator may have the formula (I):

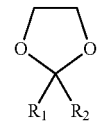

wherein R₁ is phenyl or substituted phenyl;
R₂ is phenyl, substituted phenyl or substituted alkyl;
and wherein, when each of R₁ and R₂ is phenyl or substituted phenyl, the respective phenyl groups may optionally be linked by a bridging moiety to form a structure having the following framework:

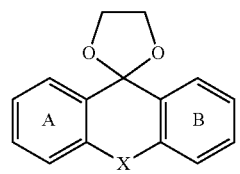

where X is S or >C=O and where each of the A and B rings may be substituted;
or wherein R₁ and R₂ may be joined to form a conjugated ring system which is optionally substituted.

In one embodiment, the protected ketone photoinitiator has the formula:

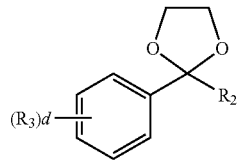

where d is 1 to 5 and where each R₃ is independently hydrogen or a substituent selected from alkyl (for example C1-4 alkyl), aryl (for example phenyl or substituted phenyl), alkylthio (eg C1-4 alkyl thio), aryl thio (for example where the aryl is phenyl or substituted phenyl, eg substituted by alkyl such as C1-4 alkyl) or heterocycle (for example morpholino); and
R₂ is phenyl or substituted phenyl or substituted alkyl.

Where R₂ is substituted phenyl the substituents on the phenyl may be selected from alkyl, or substituted alkyl, phenyl or substituted phenyl.

Where $R_2$ is substituted alkyl, the substituents may be selected from one or more of hydroxy, hydroxyalkyl, alkoxy, aryl, alkylaryl, amino, heterocycle, such as morpholino. For example, $R_2$ may be

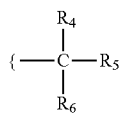

in which $R_4$, $R_5$ and $R_6$ are each independently selected from hydrogen, hydroxy, hydroxyalkyl, alkoxy, alkyl, aryl, amino or heteroaryl.

Alternatively, $R_1$ and $R_2$ may be joined to form a conjugated ring system in which the ketone of the base photoinitiator is in conjugation with at least one aromatic ring. For example, $R_1$ and $R_2$ may be joined together to form a conjugated heterocyclic ring system such as a fluorone ring system having the structure:

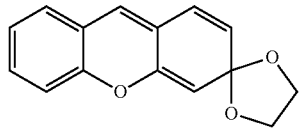 [SMILES: C1=CC2(C=C3Oc4ccccc4C=C13)OCCO2]

which may optionally be substituted.

As previously noted, the method of the invention is applicable to reactive substrates wherein the substrate comprises colour-changeable constituents, which includes chromophores per se. However, in current applications it is envisaged that the colour change will take place during a crosslinking and/or polymerisation process to enable areas at which reaction has taken place to be identified. Leuco crystal violet is an important chromophore in this respect (latent colour formers are generally termed "leuco dyes"). Other leuco dyes to which the method of the invention may be applied include leucoxanthene and leucofluorans.

Figure 5:
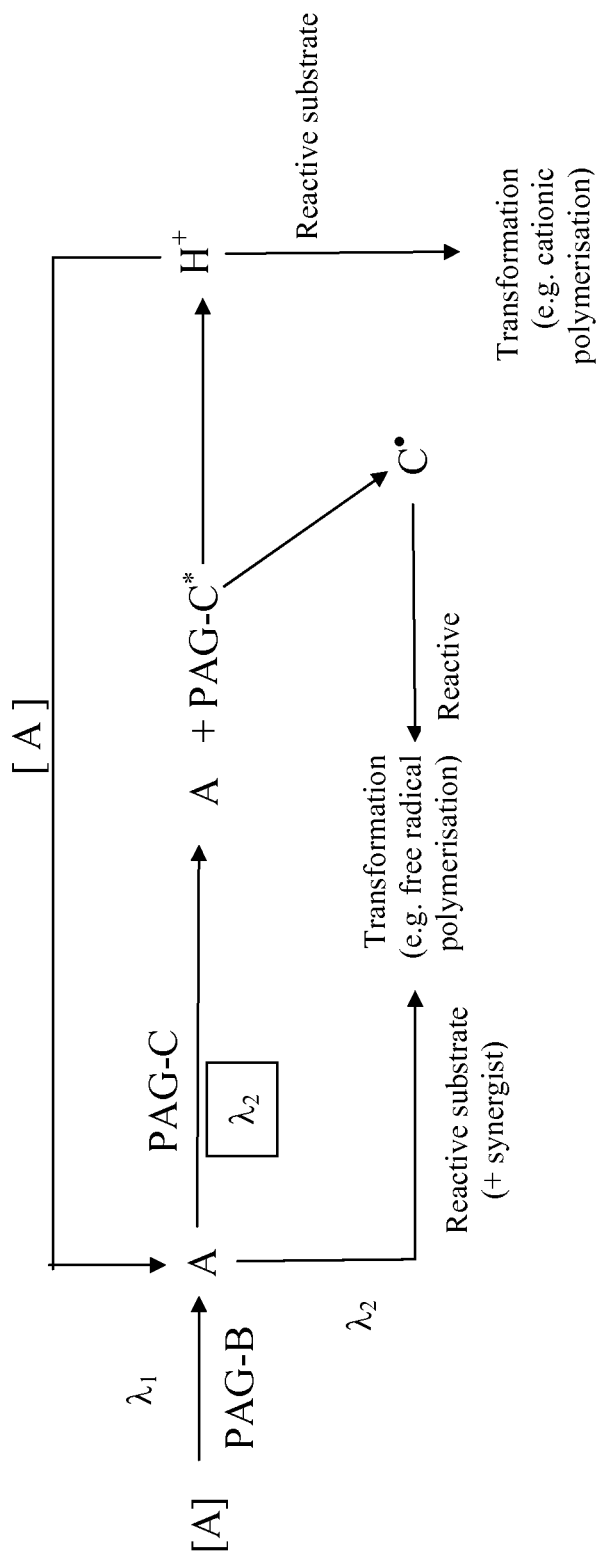
FIG. 5 illustrates a method involving use of the protected photoinitiator and two further initiator species.

With reference now to FIG. 5, and as discussed generally above, the protected, or latent, photoinitiator is most commonly to be a protected photoinitiator (initiator A) whose protection is removed in a reaction which takes place under preliminary conditions. Such preliminary conditions may include the use of another photoinitiator (initiator B), which, when exposed to electromagnetic radiation of an appropriate wavelength/energy, is able to interact with the latent photoinitiator to cause the latent photoinitiator to be converted into initiator A. The present invention will, unless otherwise indicated, be described with reference to such a mode of activating the latent photoinitiator. There is then overall use of two photoreactions which will need to include application of electromagnetic radiation at two distinct wavelengths. In particular a low power source of radiation may be employed in a first or preliminary photoreaction, which may be utilised in achieving an imagewise exposure of the substrate, and a higher dosage of radiation is applied subsequently as a flood in connection with a second photoreaction in which the reactive substrate is transformed. Preferably, a laser is used in applying the low energy source of actinic radiation imagewise. In contrast with the silver halide process described above, in which the quantum efficiency for the formation of silver atoms during the initial exposure stage is one or less; in the current invention, the quantum efficiency for the formation of initiator A, under preliminary photoreaction reactions, can be much higher than one. viz. one photon causes many protected initiator molecules to be unblocked, thereby creating many molecules of initiator A. Subsequent exposure of the substrate to actinic radiation in the second step causes initiator A to polymerise and/or crosslink the substrate and/or cause a colour change to occur in the substrate. Furthermore, by use of a carefully selected combination of initiator A and the wavelength of radiation used in the second step, initiator A can be made to interact with a third initiator (initiator C), also applied with the substrate and which does not itself absorb at the wavelength of the radiation used in the first or second step, via a sensitisation mechanism, wherein initiator C can also cause polymerisation and/or crosslinking and/or colour change to occur in the substrate as well as further unblocking of protected initiator A.

Such method embodying this invention thus also uses an auto-accelerative amplification step, in which a second photochemical reaction is carried out subsequently to a preliminary, preferably photochemical reaction.

The unsubstituted 1,3 dioxolane structure can be produced from a ketone photoinitiator starting material by the skilled person using conventional chemistry. Reference in this respect may be made to J. Chem. Soc., Perkin Trans. 1, 2001, 1807-1815 and Tetrahedron Letters 42 (2001) 1789-1791.

The dioxolane ring opening reaction is applicable to formation of a whole range of ketonic functional initiator and co-initiator species ranging from such simple well known materials as benzil dimethyl ketal through to exotic materials such as di-iodo butoxy fluorone (a viable active photoinitiator used for stereolithography). When made in the form of the required unsubstituted 1,3 dioxolanes, the resulting compounds act as "latent photoinitiators", capable of being activated by thermal acid generators or by low doses of light on formation of catalytic quantities of acid from cationic initiators. Examples of such ketone photoinitiators are:

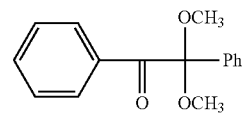
2,2-dimethoxy-2-phenyl acetophenone

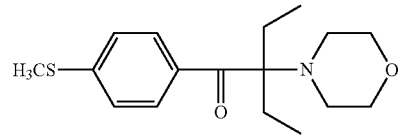
2-methyl-1-[4-(methylthio)phenyl-2-morpholino propan-1-one

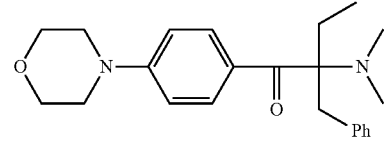
2-benzyl-2-N,N-dimethylamino-1-(4-morpholinophenyl-1-butanone

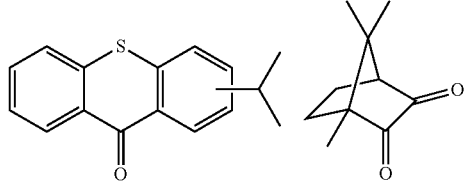
Isopropylthioxanthone          Camphorquinone

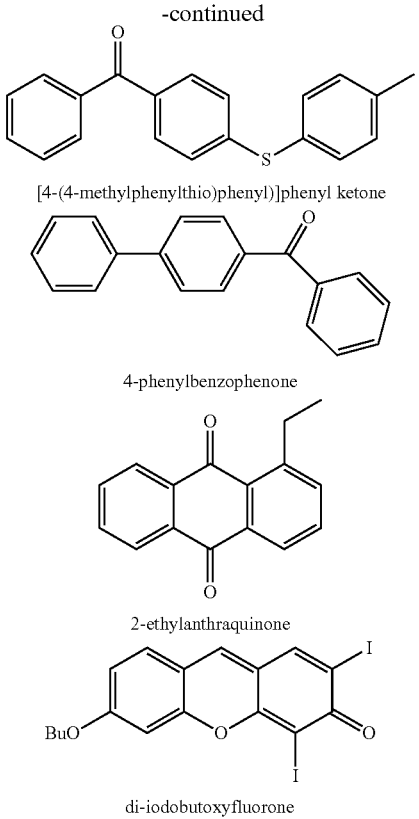

[4-(4-methylphenylthio)phenyl)]phenyl ketone 4-phenylbenzophenone 2-ethylanthraquinone di-iodobutoxyfluorone Other ketone photoinitiators which may be used as the basis for preparing a protected photoinitiator are diphenyl ketone, diethoxyacetophenone, 1-hydroxy-cyclohexyl-phenyl ketone, 2-hydroxy-2-methyl-1-phenyl-propan-1-one, various benzoin ethers, as well as diethoxyacetophenone and 1-hydroxycyclohexyl phenyl ketone, and 2-hydroxy-2-methyl-1-phenylpropan-1-one and ethers thereof.

By way of example, the ketone photoinitiator which is to be protected in accordance with the present invention may be selected from the following publications, which may overlap in their disclosure. Any reference to a species in these lists which is not a ketone photoinitiator is unintended, and should be disregarded:

Photoinitiators Disclosed in U.S. Pat. No. 7,585,611B benzoin and benzoin alkyl ethers such as benzoin, benzoin methyl ether, benzoin ethyl ether, and benzoin isopropyl ether;

acetophenones such as acetophenone, 2,2-dimethoxy-2-phenyl acetophenone, 2,2-diethoxy-2-phenyl acetophenone, and 1,1-dichloroacetophenone;

aminoacetophenones such as 2-methyl-1-[4-(methylthio) phenyl]-2-morpholinoaminopropanone-1,2-benzyl-2-dimethylamino-1-(4-morpholinophenyl)butan-1-one, and N,N-dimethyl aminoacetophenone;

anthraquinones such as 2-methylanthraquinone, 2-ethylanthraquinone, 2-t-butyl-anthraquinone, and 1-chloroanthraquinone;

thioxanthones such as 2,4-dimethylthioxanthone, 2,4-diethylthioxanthone, 2-chlorothioxanthone and 2,4-diisopropylthioxanthone;

ketals such as acetophenone dimethyl ketal and benzyl dimethyl ketal;

benzophenones or xanthones such as benzophenone and 4,4'-bisdiethylaminobenzophenone;

2,4,6-trimethylbenzoyl diphenyl phosphine oxide.

Photoinitiators Disclosed in EP-1487888A

Benzoins;

benzoin ethers, such as benzoin, benzoin methyl ether, benzoin ethyl ether and benzoin isopropyl ether, benzoin phenyl ether and benzoin acetate;

acetophenones, such as acetophenone, 2,2-dimethylacetophenone and 1,1-dichloroacetophenone;

benzil, benzil ketals, such as benzil dimethyl ketal and benzil diethyl ketal;

2-methyl-1-(4 methylthiophenyl)-2-morpholino-1-propanones, which are commercially available under the name Irgacure®;

anthraquinones, such as 2-methylanthraquinone, 2-ethylanthraquinone, 2-tert-butylanthraquinone, 1-chloroanthraquinone and 2-amylanthraquinone, triphenylphosphine, benzoylphosphine oxide (Luzirin TPO, BASF);

benzophenones, such as benzophenone and 4,4'-bis(N,N'-dimethylamino)benzophenone, thioxanthones and xarnthones, 1-phenyl-1,2-propandione 2-O-benzoyloxime 1-aminophenyl ketones;

1-hydroxyphenyl ketones, such as 1-hydroxycyclohexyl phenyl ketone, phenyl 1-hydroxyisopropyl ketone and 4-isopropylphenyl-hydroxyisopropyl ketone, and 2-benzyl-2,2-dimethylamino-1-(4-morpholinophenyl)-1-butanone, Photoinitiators Disclosed in U.S. Pat. No. 7,425,585B A photoinitiator of the formula:

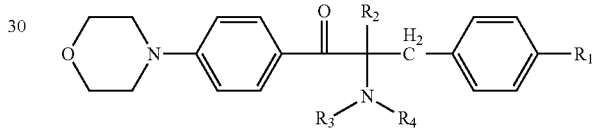

$R_1$ is linear or brandied $C_1$-$C_{12}$ alkyl;
$R_2$ is linear or brandied $C_1$-$C_4$ alkyl;
$R_3$ and $R_4$ independently of one another are linear or branched $C_1$-$C_8$ alkyl $C_1$-$C_{12}$ alkyl is linear or branched and is for example $C_1$-$C_{10}$, $C_1$-$C_8$, $C_1$-$C_6$, $C_1$-$C_4$, $C_6$-$C_{10}$, $C_8$-$C_{10}$, $C_6$-$C_8$, $C_4$-$C_8$ or $C_4$-$C_{10}$ alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl and dodecyl.

$R_1$ is for example linear or branched $C_1$-$C_4$ alkyl, in particular methyl, ethyl, isopropyl, n-propyl, isobutyl and n butyl. $R_1$ is for example methyl, ethyl or propyl, in particular ethyl and $R_3$ and $R_4$ in particular independently of one another are linear or branched $C_1$-$C_4$ alkyl, in particular methyl.

Examples are

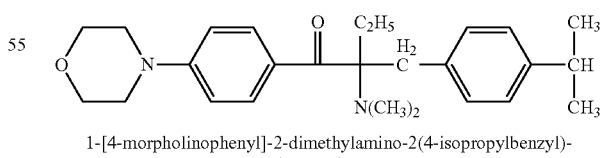

1-[4-morpholinophenyl]-2-dimethylamino-2(4-isopropylbenzyl)-butane-1-one

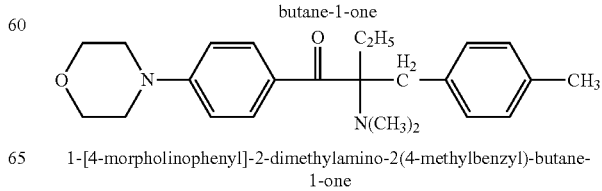

1-[4-morpholinophenyl]-2-dimethylamino-2(4-methylbenzyl)-butane-1-one

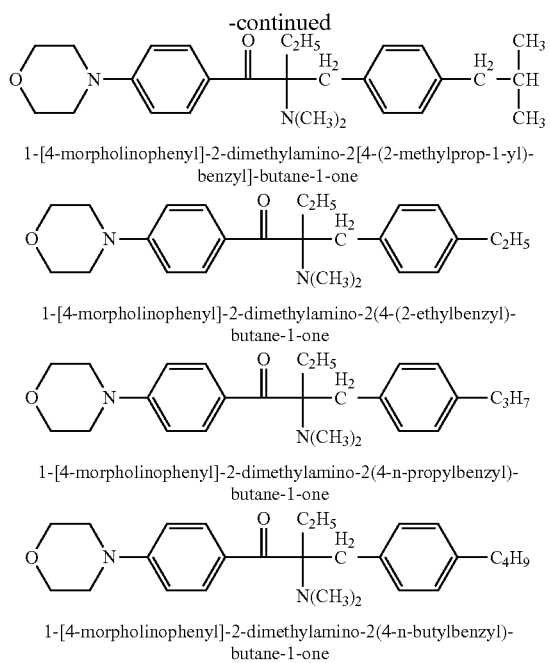

1-[4-morpholinophenyl]-2-dimethylamino-2[4-(2-methylprop-1-yl)-benzyl]-butane-1-one 1-[4-morpholinophenyl]-2-dimethylamino-2(4-(2-ethylbenzyl)-butane-1-one 1-[4-morpholinophenyl]-2-dimethylamino-2(4-n-propylbenzyl)-butane-1-one 1-[4-morpholinophenyl]-2-dimethylamino-2(4-n-butylbenzyl)-butane-1-one Further examples of photoinitiators disclosed in U.S. Pat. No. 7,425,585B are 1. Thioxanthones Thioxanthone, 2-isopropylthioxanthone, 2-chlorothioxanthone, 2-dodecylthioxanthone, 2,4-diethylthioxanthone, 2,4-dimethylthioxanthone, 1-methoxycarbonylthioxanthone, 2-ethoxycarbonylthioxanthone, 3-(2-methoxyethoxycarbonyl)-thioxanthone, 4-butoxycarbonylthioxanthone, 3-butoxycarbonyl-7-methylthioxanthone, 1-cyano-3-chlorothioxanthone, 1-ethoxycarbonyl-3-chlorothioxanthone, 1-ethoxycarbonyl-3-ethoxythioxanthone, 1-ethoxycarbonyl-3-aminothioxanthone, 1-ethoxycarbonyl-3-phenylsulfuryl-thioxanthone, 3,4-di-[2-(2-methoxyethoxy)-ethoxycarbonyl]-thioxanthone, 1-ethoxycarbonyl-3-(1-methyl-1-morpholinoethyl)-thioxane, 2-methyl-6-dimethoxymethyl-thioxanthone, 2-methyl-6-(1,1-dimethoxybenzyl)-thioxanthone, 2-morpholinomethylthioxanthone, 2-methyl-6-morpholinomethylthioxanthone, N-allylthioxanthone-3,4-dicarboximide, N-octylthioxanthone-3,4-dicarboximide, N-(1,1,3,3-tetramethylbutyl)-thioxanthone-3,4-dicarboximide, 1-phenoxythioxanthone, 6-ethoxycarbonyl-2-methoxythioxanthone, 6-ethoxycarbonyl-2-methylthioxanthone, thioxanthone-2-carboxylic acid polyethyleneglycol ester, 2-hydroxy-3-(3,4-dimethyl-9-oxo-9H-thioxanthon-2-yloxy)-N,N,N-trimethyl-1-propanaminium chloride;

2. Benzophenones benzophenone, 4-phenyl benzophenone, 4-methoxy benzophenone, 4,4'-dimethoxy benzophenone, 4,4'-dimethyl benzophenone, 4,4'-dichlorobenzophenone 4,4'-bis(dimethylamino)-benzophenone, 4,4'-bis(diethylamino)benzophenone, 4-methyl benzophenone, 2,4,6-trimethylbenzophenone, 4-(4-methylthiophenyl)-benzophenone, 3,3'-dimethyl-4-methoxy benzophenone, methyl-2-benzoylbenzoate, 4-(2-hydroxyethylthio)benzophenone, 4-(4-tolylthio)-benzophenone, 4-benzoyl-N,N,N-trimethylbenzenemethanaminium chloride, 2-hydroxy-3-(4-benzoylphenoxy)-N,N,N-trimethyl-trimethyl-1-propanaminium chloride monohydrate, 4-(13-acryloyl-1,4,7,10,13-pentaoxatridecyl)-benzophenone, 4-benzoyl-N,N-dimethyl-N-[2-(1-oxo-2-propenyl)oxy]ethyl-benzenemethanaminium chloride;

3. Coumarins

Figure 6:
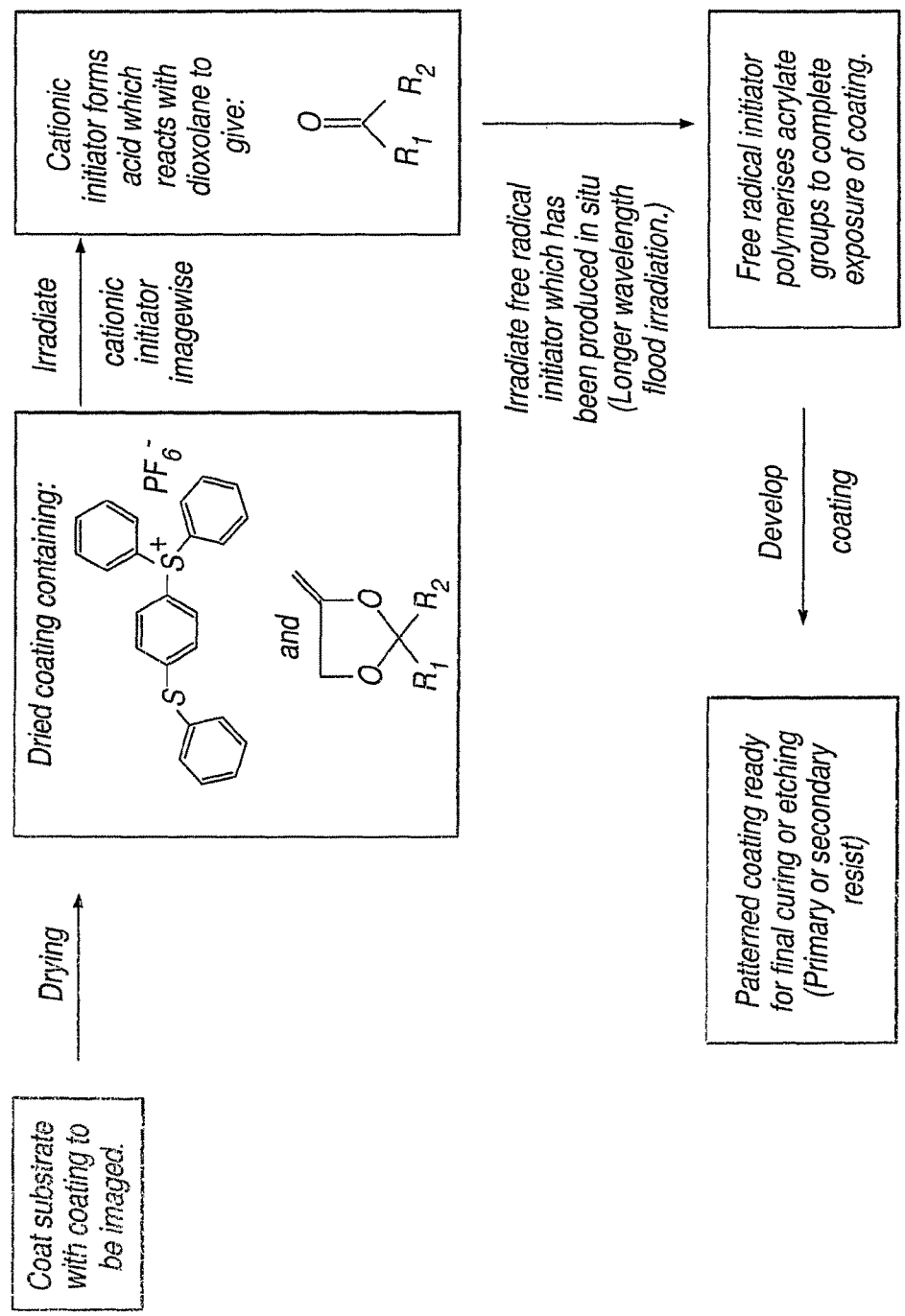
FIGS. 6 to 9 illustrate photopolymerization methods of the invention.

Coumarin 1, Coumarin 2, Coumarin 6, Coumarin 7, Coumarin 30, Coumarin 102, Coumarin 106, Coumarin 138, Coumarin 152, Coumarin 153, Coumarin 307, Coumarin 314, Coumarin 314T, Coumarin 334, Coumarin 337, Coumarin 500, 3-benzoyl coumarin, 3-benzoyl-7-methoxycoumarin, 3-benzoyl-5,7-dimethoxycoumarin, 3-benzoyl-5,7-dipropoxycoumarin, 3-benzoyl-6,8-dichlorocoumarin, 3-benzoyl-6-chloro-coumarin, 3,3'-carbonyl-bis[5,7-di(propoxy)coumarin], 3,3'-carbonyl-bis(7-methoxycoumarin), 3,3'-carbonyl-bis(7-diethylamino-coumarin), 3-isobutyroylcoumarin, 3-benzoyl-5,7-dimethoxy-coumarin, 3-benzoyl-5,7-diethoxy-coumarin, 3-benzoyl-5,7-dibutoxycoumarin, 3-benzoyl-5,7-di(methoxyethoxy)-coumarin, 3-benzoyl-5,7-di(allyloxy)coumarin, 3-benzoyl-7-dimethylaminocoumarin, 3-benzoyl-7-diethylaminocoumarin, 3-isobutyroyl-7-dimethylaminocoumarin, 5,7-dimethoxy-3-(1-naphthoyl)-coumarin, 5,7-diethoxy-3-(1-naphthoyl)-coumarin, 3-benzoylbenzo[f]coumarin, 7-diethylamino-3-thienoylcoumarin, 3-(4-cyanobenzoyl)-5,7-dimethoxycoumarin, 3-(4-cyanobenzoyl)-5,7-dipropoxycoumarin, 7-dimethylamino-3-phenylcoumarin, 7-diethylamino-3-phenylcoumarin, the coumarin derivatives disclosed in JP 09-179299-A and JP 09-325209-A, for example 7-[{4-chloro-6-(diethylamino)-S-triazine-2-yl}amino]-3-phenylcoumarin;

4. 3-(aroylmethylene)-thiazolines 3-methyl-2-benzoylmethylene-β-naphthothiazoline, 3-methyl-2-benzoylmethylene-benzothiazoline, 3-ethyl-2-propionylmethylene-β-naphthothiazoline;

5. Rhodanines 4-dimethylaminobenzalrhodanine 4-diethylaminobenzalrhodanine, 3-ethyl-5-(3-octyl-2-benzothiazolinylidene)-rhodanine, the rhodanine derivatives, formulae [1], [2], [7], disclosed in JP 08-305019A;

6. Other Compounds acetophenone, 3-methoxyacetophenone, 4-phenylacetophenone, benzil, 4,4'-bis(dimethylamino)benzil, 2-acetylnaphthalene, 2-naphthaldehyde, dansyl acid derivatives, 9,10-anthraquinone, anthracene, pyrene, aminopyrene, perylene, phenanthrene, phenanthrenequinone, 9-fluorenone, dibenzosuberone, curcumin, xanthone, thiomichler's ketone, α-(4-dimethylaminobenzylidene) ketones, 2,5-bis(4-diethylaminobenzylidene)cyclopentanone, 2-(4-dimethylamino-benzylidene)-indan-1-one, 3-(4-dimethylamino-phenyl)-1-indan-5-yl-propenone, 3-phenylthiophthalimide, N-methyl-3,5-di(ethylthio)-phthalimide, N-methyl-3,5-di(ethylthio)phthalimide, phenothiazine, methylphenothiazine, amines, e.g. N-phenylglycine, ethyl 4-dimethylaminobenzoate, butoxyethyl 4-dimethylaminobenzoate, 4-dimethylaminoacetophenone, triethanolamine, methyldiethanolamine, dimethylaminoethanol, 2-(dimethylamino)ethyl benzoate, p-dimethylaminobenzoate, An example of a photopolymerisation method embodying this invention typically involves an initial irradiation of a film containing a cationic (acid producing) photoinitiator, acrylate and unsubstituted 1,3 dioxolane-based latent photoinitiator. This irradiation is fast and efficient, as the polymer formed in this step may be minimal and not cause any vitrification, which is a prime limit on reaction rates. The acid produced by the cationic initiator causes the dioxolane group to be removed and the underlying photoinitiator to be generated. Subsequent to the low energy image-wise exposure, the system can be flood irradiated with light of wavelength outside the absorption range of the cationic initiator so as to avoid further photolysis and acid formation, but within the absorption range of the initiator formed from the cleavage of the dioxolane ring, such that the initiator so formed can cause polymerisation and/or crosslinking and/or colour change to occur in the substrate where it has been formed. This irradiation is not image-wise and therefore can involve far higher dosages of light in a relatively short time. An application for this example is that of laser direct imaging of photoimageable coatings. The technology eliminates the bottleneck of having to deliver all of the polymerisation energy via the laser in an image-wise fashion. An example of this technology is summarised in the flow scheme of FIG. 6 of the accompanying drawings.

Preferably in general, cationic acid-producing species such as sulphonium and iodonium salts and salt-form organometallic compounds are utilised in achieving conversion of the protected photoinitiator although α-sulphonyloxyketones can also be used as cationic acid-producing species. These compounds are exemplified by the following:

bis[4-(diphenylsulphonio)-phenyl]sulphide bis-hexafluorophosphate or bis-hexafluoroantimonate which may optionally be in combination with a mono- or poly-[4-(phenylthiodiphenyl)]sulphonium hexafluorophosphate or hexafluoroantimonate;

bis[4-(di(4-(2-hydroxyethyl)phenyl)sulphonio-phenyl]sulphide bis-hexafluorophosphate;

bis[4-(di(4-(2-hydroxyethyl)phenyl) sulphonio)-phenyl]sulphide bis-hexafluoroantimonate;

($\eta^6$-2,4-(cyclopentadienyl)[(1,2,3,4,5,6-$\eta$)-(methylethyl) benzene]-iron(II) hexafluorophosphate;

4-isopropyl-4-methyl diphenyliodonium hexafluorophosphate;

diphenyliodonium hexafluorophosphate;

4-isopropyl-4-methyl diphenyliodonium tetrakis-(penta-fluorophenyl)borate;

diphenyliodonium tetrakis-(penta-fluorophenyl)borate and;

2'-hydroxy-2-phenyl-3-toluenesulphonyloxypropiophenone.

A wide range of formulations is possible. Preferably, for the acid-producing photoinitiator, the amount employed is up to 5% by weight, for example in the range of from 0.25 to 5% by weight of the material to be acted on. For the protected photoinitiator, the practical working range is up to 10%, for example from 0.25 to 10% by weight of the substrate to be acted on. In an embodiment, the amount of protected photoinitiator may be in the range of 3-10% by weight of the substrate.

While it is unlikely that this process will be able to completely match the overall silver halide process in terms of photosensitivity, nonetheless it permits products to be obtained which dramatically increase the productivity of imaging processes dependent on curing by electromagnetic radiation. Practical experience has shown that it is particularly convenient to work in the UV range. With the unsubstituted 1, 3 dioxolane latent photoinitiators and the aforementioned acid-producing photoinitiators, one can use UV irradiation of a relatively short wavelength in the first photochemical reaction and UV irradiation of a longer wavelength in the second photochemical reaction, or vice versa.

Figure 7:
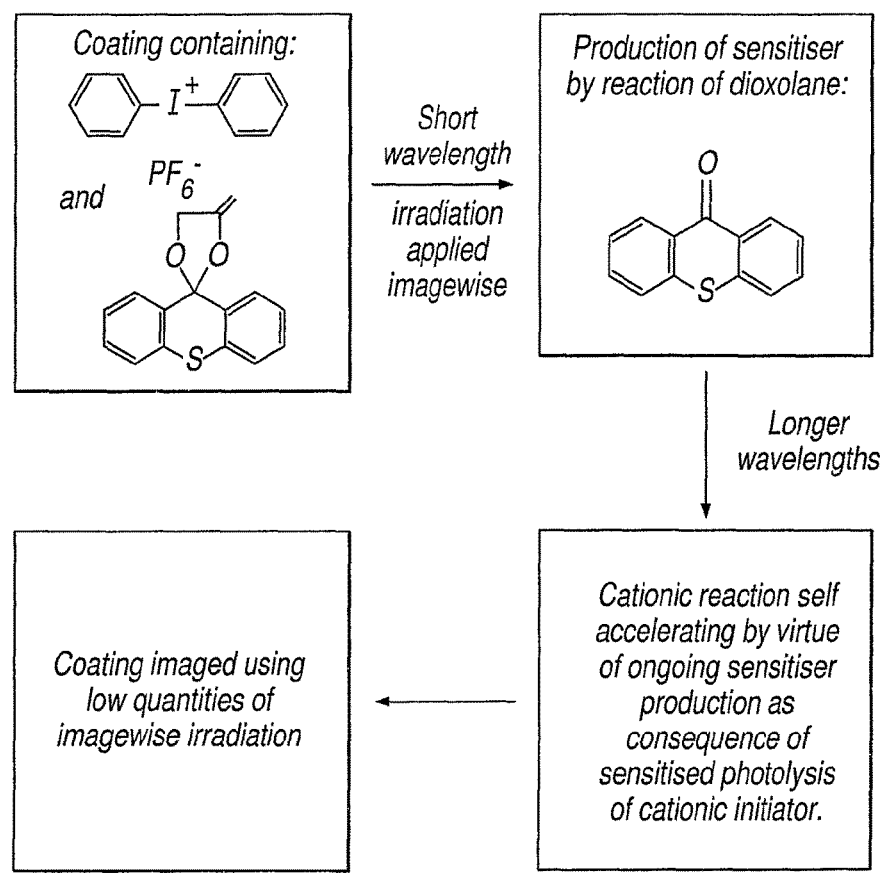

A second procedure embodying this procedure is in the field of photoimageable inks for sequential build-up (SBU) where cationic systems are to be preferred due to their advantageous physical properties. This procedure demonstrates the versatility of the method of the invention. One of the materials which can be made in protected form where the ketone is protected by an unsubstituted dioxolane ring is isopropylthioxanthone (ITX). Thioxanthones are particularly suitable as sensitizers for iodonium salts. As the iodonium salts themselves are generators of acid catalysts for cationic polymerisation, the possibility of their being used in a self-sensitizing system is apparent and provides a means of increasing quantum yields. Initial irradiation of the iodonium salt directly in an image-wise fashion results in production of a small amount of acid polymerisation catalyst. The resulting film is sensitive to an auto-accelerative reaction when flood irradiated with near visible radiation. This enhanced sensitivity opens the way for using laser direct imaging with photoimageable SBU dielectric. An example of this technology is summarised in the flow scheme of FIG. 7 of the accompanying drawings.

Figure 8:
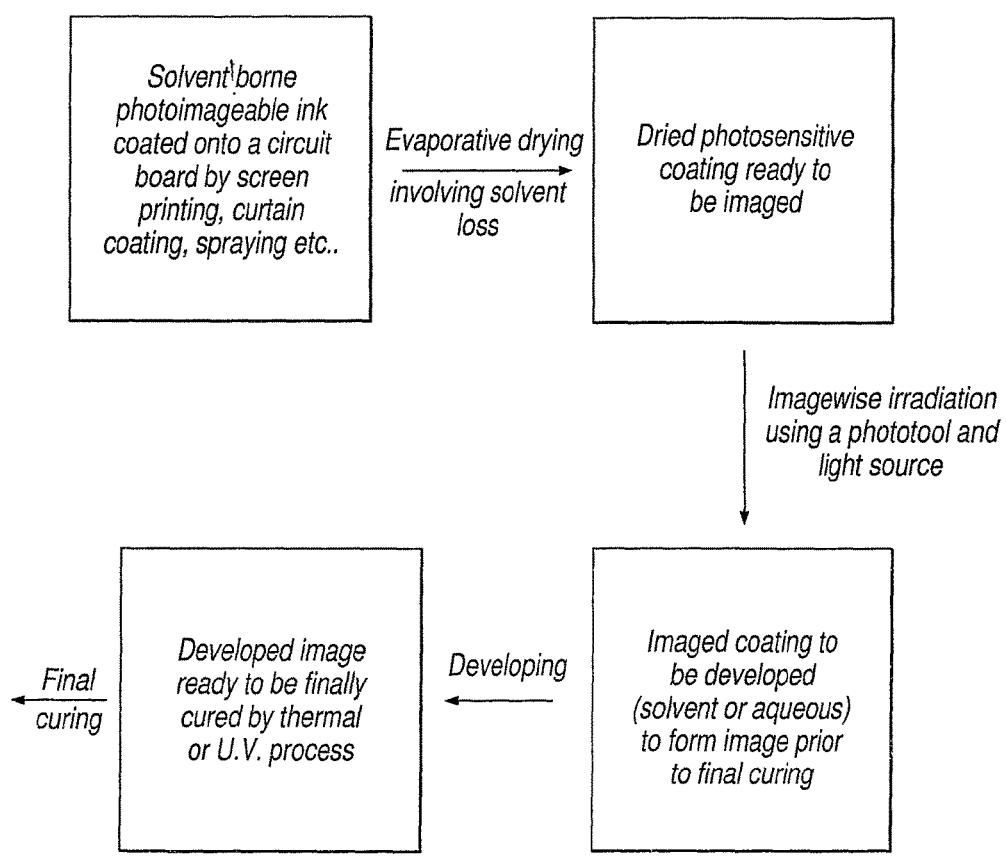

As the number of boards produced by the printed circuit board industry has increased, so have concerns over the environmental impact of board manufacturing processes, especially with regards to the emission of vapours which are difficult to contain or collect and reprocess. A process responsible for generating organic vapour emissions is the application, by various coating methods, of Liquid Photoimageable Solder masks (LPISM). In this process, the PCB is completely coated with a solvent-containing liquid formulation. After coating, the boards are dried in an oven to evaporate the solvent and produce a tack-free, photosensitive coating. Image-wise exposure of the coating and subsequent developing, either by aqueous carbonate or organic solvents allows formation of openings in the mask for purposes of component or connector placement. This technology is summarised in the flow scheme of FIG. 8 of the accompanying drawings. In the face of increasingly stringent regulatory requirements, control technology to reduce or eliminate vapour emissions, particularly during the drying stage, will become necessary. A few manufacturers have ventured to introduce waterbased LPISMs into the market place but these appear to be technically inferior to traditional solvent based products.

Figure 9:
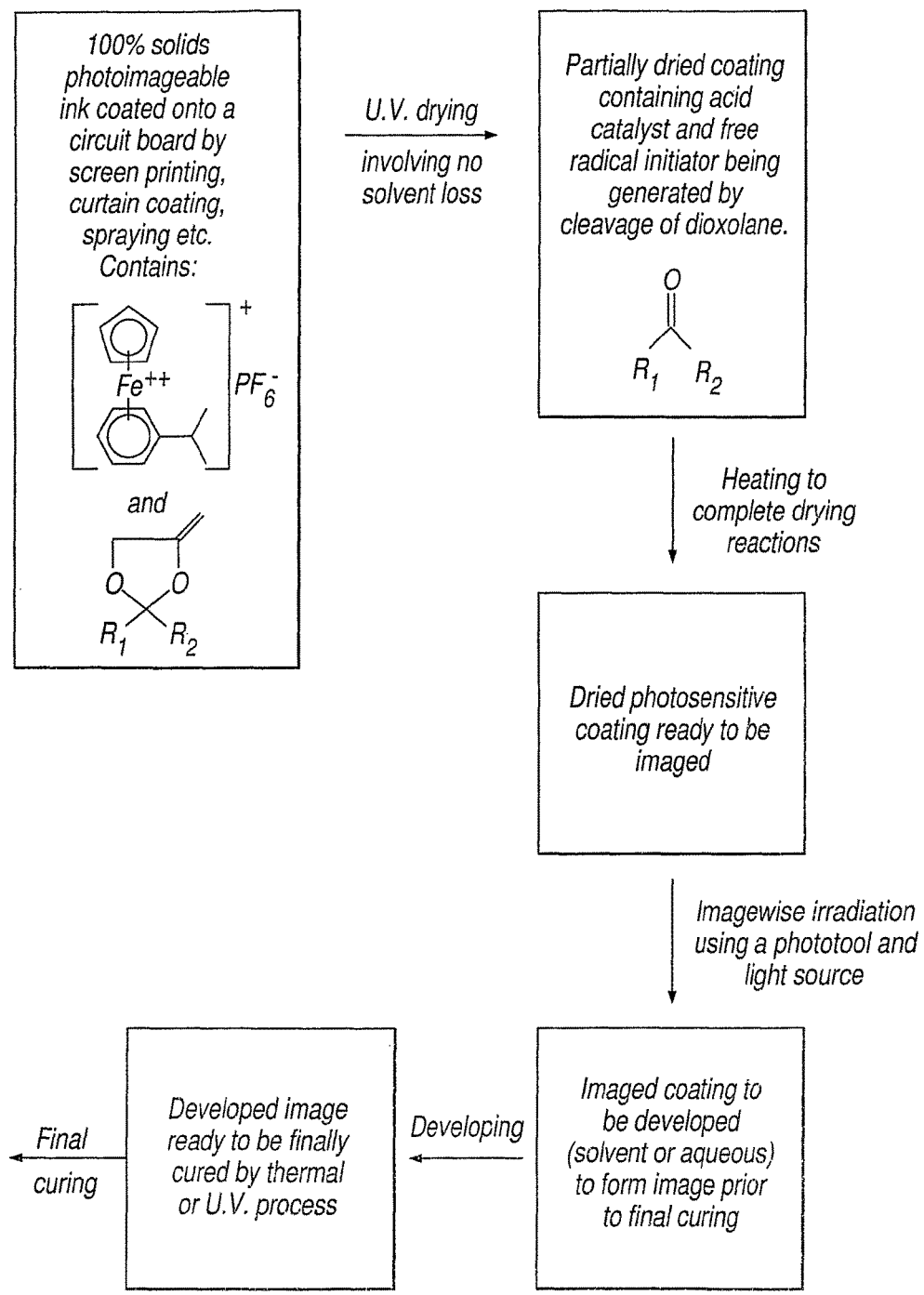

Use of a photoacid generating initiator (cationic initiator) in conjunction with a dioxolane blocked free radical initiator permits formulation of a 100% solids LPISM. This system has the advantage of containing no solvent and therefore producing no emissions. Such a 100% solids formulation, which can be made tack-free on exposure to acid catalysts, but whilst remaining developable in a suitable medium, can be made by following the teaching of the current invention. The LPISM thus produced can be UV dried, being heated to complete the solidification process and to ensure complete deblocking. Subsequently it can be re-exposed to image the formulation and still be developed and finally cured in a fashion familiar to the industry. The use of dioxolane blocked latent photoinitiators preserves the radical initiator during the imaging step whilst the coating is UV dried. The process sequence is shown by the flow diagram in FIG. 9.

A variety of approaches can be used to effect the UV drying. Vinyl ethers, cycloaliphatic epoxides and oxetane compounds can be used as polymerisable solvents. Alternatively, use of such materials as cross linkers for functionalised resins is viable. Use of reactive resins, and building resin molecular weight by cationic reaction can also be used. Finally, it is possible to use a vinyl ether functional resin and react it under cationic conditions with a hydroxy functional solvent or vice versa. Such technology may be represented by the following:

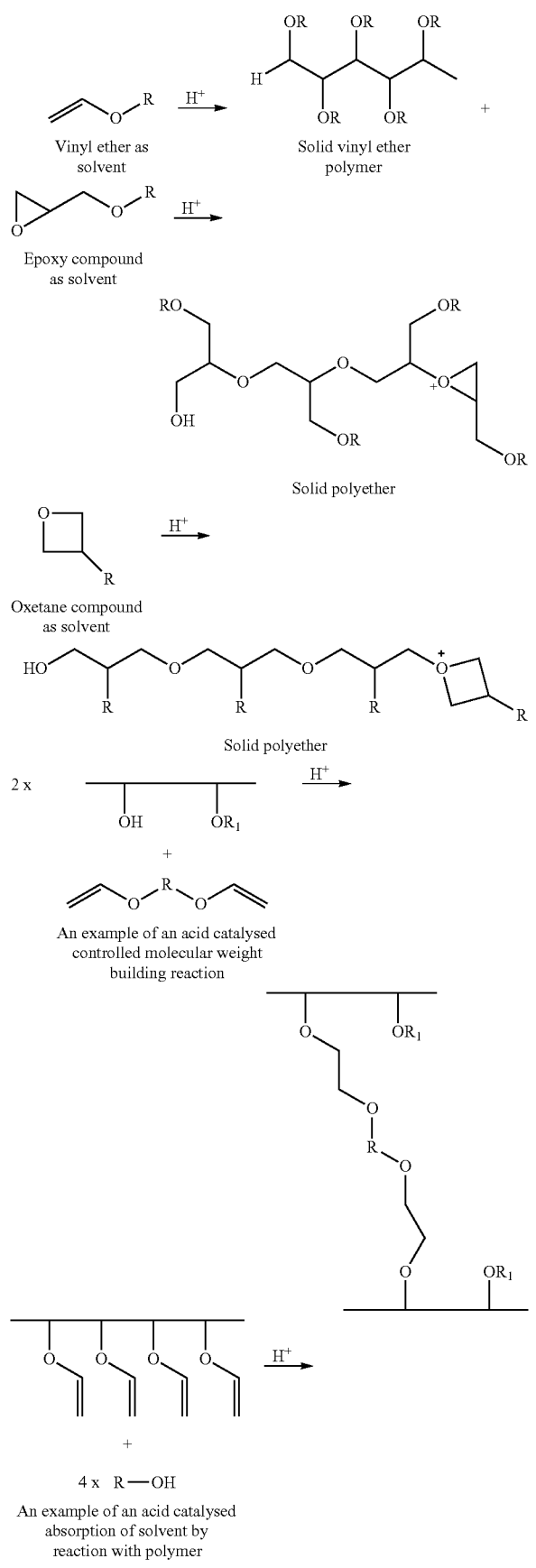

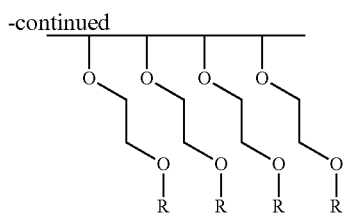

Similar applications are found in the manufacture of flexographic printing plates and other imaged printing systems.

A further example of the use of latent photoinitiators is in the field of visible light active photoinitiators. The use of these initiators requires the working areas to be configured as "red light" zones, which provide an exceedingly difficult environment to work in. By using the use of this invention to produce blocked, visible light photoinitiators, formulations can be produced, which become sensitive to visible light only after activation. Substantial production and handling benefits ensue from this.

Yet another application is in the curing of thick clear films in conjunction with high intensity excimer lamp technology. A low concentration of initiator, whilst necessary for minimising optical density in thick coatings, is not normally adequate to effect polymerisation. Thus the choice of photoinitiator used for the curing of thick films is limited to those which undergo photobleaching e.g. acylphosphine oxides. With careful formulation, use of a low concentration of cationic initiator in conjunction with a dioxolane blocked free radical initiator, results in the ongoing, in-situ formation of free radical initiator during irradiation by UV light. Thus, because the light absorption of dioxolane protected initiators is at shorter wavelength than their parent initiator, optical density can be controlled with only a small amount of free radical initiator being present at any time. High intensity excimer lamps are particularly suitable for this application as the near monochromatic output of the excimer lamps is capable of photolysing low concentrations of short wavelength sensitive cationic initiators in very thick clear films.

The latent initiators described here are not confined to being unblocked by photochemical processes yielding acid moieties. Any blocked acid of sufficient strength, for example a blocked toluenesulphonic acid, especially p-toluenesulphonic acid, will, on unblocking, catalyse the breakdown of the dioxolane ring on the latent photoinitiators. Examples of such compounds that can be used are the blocked superacids produced by King Industries. These can be unblocked thermally and can be useful for a number of the examples given here, especially the 100% solids LPISM and give improved handling for viable initiated processes.

In summary, the chemistry outlined here provides for the synthesis of a blocked photoinitiator by a prescribed synthetic method, for example by reaction of a carbonyl group to form a dioxolane ring, as latent photoinitiator.

The technology is useful in the following applications:

1. Primary and secondary imaging (PCB industry).
2. UV initiated sensitisation of visible initiators.
3. Making visible active formulations easy to handle.
4. Controlling the cure of thick films.
5. Improving shelf life of UV curing formulations.

EXAMPLES

Example 1

Preparation of 1,3 dioxolane protected 2-isopropylthioxanthone (DITX)

To a 5000 ml, 3-necked, round-bottomed flask equipped with overhead mechanical stirrer, reflux condenser connected to a sodium hydroxide scrubber and Nitrogen inlet was dissolved a solution of 2-ITX (700 g, 2.752M) in Thionyl chloride (3262 g, 2000 ml, 27.42M, 10 Mol eq's). Under a Nitrogen stream this wine-red solution was heated to reflux (internal temp=80° C.) with stirring for 4.5 hours. The reaction mixture was cooled to ambient overnight under a positive pressure of Nitrogen. The wine red reaction mixture was transferred to a rotorvapor and excess Thionyl chloride was removed under reduced pressure (water bath temperature was maintained at 40° C.). The mobile oil was taken up in Toluene (1050 ml) and then added drop wise, under a Nitrogen atmosphere, over 1.5 hour, to a previously prepared and vigorously stirred solution of Sodium methoxide (595 g, 11.014M, 4.0 Mol eq's) in Methanol (2100 ml) at such a rate as to keep the vessel temperature between 0-10° C. Once addition was complete, the cooling bath was removed and the vessel contents allowed to warm to ambient over 1 hour.

Tap water was added to the cooling bath and stirring continued for a further hour. The reaction mixture was then transferred to a rotorvapor and Methanol removed under reduced pressure. The resulting residue was quenched into a vigorously stirred mixture of Toluene (1.0 L) and Water (3.5 L). Stirring was continued for 20 minutes at ambient and the reaction mixture was then transferred to a separating funnel and allowed to settle over 15 minutes. The Toluene layer was back washed with Water (1.75 L) and allowed to separate. The upper Toluene layer was removed from the separator, dried over sodium sulphate and stored in the freezer overnight. The Toluene solution was then filtered through Celite and the resulting orange/brown filtrate was transferred to a rotorvapor and Toluene removed under reduced pressure to give crude 9,9-Dimethoxy-2isopropylthioxanthone as a pale brown oil.

To the crude 9,9-Dimethoxy-2-ITX oil (2848 g, 9.48M) was added THF (2.4 L), camphor sulphonic acid (39.0 g, 0.1678M, 1.7 Mol %) and ethylene glycol (1536 g, 1380 ml, 24.74M, 2.6 Mol eq) and stirring was commenced at ambient. Stirring was continued over the weekend where a completion check revealed that all the 9,9-dimethoxy-2-ITX had been consumed. The reaction mixture was then transferred to a rotorvapor and organics removed under reduced pressure (bath at 40° C.). The cooled distillation residue was dissolved in DCM (4.0 L) and back washed with 5% Sodium bicarbonate solution (2×4.0 L) and Water (2×5.0 L). The organic layer was then dried over sodium sulphate, filtered through Celite, cake washed with DCM (1×1.0 L) and filtrate stripped to a brown oil on the rotorvapor (water bath=40° C. 10 mbar).).

The crude oil was purified during work up to remove unreacted starting material, dissolved in Toluene (10 L) and then filtered through basic alumina (3 Kg) (pre-washed with Toluene (10 L)). A total of three filtrations were carried out where the basic alumina was regenerated between filtrations by washing with DCM (2 L), Methanol (2×2 L) and finally Toluene (1×5 L). The resulting filtrate was concentrated on the rotorvapor to approx half volume, polish filtered through GF/F filter paper (to remove alumina fines) and then returned to the rotorvapor and further concentrated to a pale amber oil (water bath=55° C.@15 mbar). Yield of crude DITX oil=2250 g. GC purity indicated 65.5% product (DITX) and 28% reduced alcohol. The crude oil was then warmed to 40° C. in pre-treated Ethanol* (2.5 L) and the resulting solution was allowed to cool, with stirring, to ambient temperature where crystallisation of DITX was observed. The pale yellow solid was washed with cold ethanol (2×1.0 L) and pulled dry on the filter. The damp weight of pure DITX was 1225 kg. The off-white material was air dried in the fume hood over 48 hours to give pure DITX in an overall yield of 1078 g, 37.5% from 2-ITX.

Analysis of DITX

Appearance: Off-white solid
Purity (G.C): 99.2%
T.l.c. (Petrol 9:1 Ethyl acetate): Product spot @ Rf=0.40+
 Two Faint impurity spots @ Rf=0.07+0.01
Solution (5% DCM): Clear colourless solution
Mp. 70-72° C. (Sharp)
IH nmr: (CDCl3): Conforms to structure
CHN: Found: C, 72.45%, H, 6.09%.
 Theory: C, 72.45%, H, 6.08%.

Example 2

The use of DITX prepared in Example 2 was tested as a protected photoinitiator in comparison with a protected ITX in which the protecting group was a methylene 1,3 dioxolane group was tested and a protected ITX in which the protecting group was a chloromethylene 1,3 dioxolane group.

The test sample of dioxolane was employed at a level of 5% in a formulation which also contained 3% of aryl iodonium hexafluorophosphate, 80% of an acrylated and carboxylated epoxy novolac resin (65% solids) and 12% of a difunctional acrylic monomer.

The test formulations were coated in duplicate onto standard microscope slides using a gap-bar type coater with a gap of approximately 200 microns. The coater deposited a wet thickness of approximately 100 microns.

The UV spectrum of each test sample was recorded before drying, and the absorbance at 385 nm recorded. All samples were then dried at 80 C for 20 minutes, and the UV spectrum recorded again. Any increase in absorbance at 385 nm was noted. This measurement reflects the stability to drying of the test dioxolane in a formulation.

One slide of each test formulation was then subjected to 6 minutes irradiation using a UV Process Supply 415 nm LED lamp array from a distance of approximately 1 cm.

Again the UV spectrum of the irradiated samples was recorded and any increase in absorbance at 385 nm recorded. This measurement also reflects the stability of the dioxolane but is more sensitive as it allows for amplification of any ITX produced. It also demonstrates stability of formulation to 415 nm light.

The second slide for each test formulation which exhibited stability to 415 nm irradiation was subjected to 15 seconds exposure to a low pressure mercury grid lamp radiating principally at 254 nm, positioned 20 mm from the coating surface.

The rate of increase of absorbance at 385 nm was measured and the sample subjected to irradiation at 415 nm for 2 minutes, subsequent to which the rate of increase of absorbance at 385 nm was re-measured. Any positive change in the rate of increase reflects the amplification effect.

The results obtained are set forth in Table 1 below.

|  | Protecting group on ITX | | |
| --- | --- | --- | --- |
|  | methylene 1,3 dioxolane | 13, dioxolane | chloromethylene 1,3 dioxolane |
| Stable to drying in formulation? | No. | Yes. | Yes. |
| Stable to 415 nm? | No. (ITX formed at drying) | Yes. | Yes. |
| Response to 254 nm? | N/A | Yes. | Minimal. |
| Amplification by 415 nm? | N/A | Rapid. | Slight. |
| All tests passed? | No. | Yes. | Yes. (But performance poor) |

The methylene 1,3 dioxolane functional blocked initiator is unstable in carboxylic acid containing formulations which may limit its utility for some applications. The chloromethylene dioxolane demonstrates that alternative substituted dioxolanes are more stable but have poor performance. The simple dioxolane is unexpectedly superior in terms of stability and deketalisation.

The invention claimed is:

1. A method for the photoinitiated transformation of a transformable reactive substrate, said method including:
    an initial step in which a protected ketone photoinitiator species having the formula:

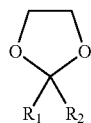

wherein $R_1$ is phenyl or substituted phenyl; $R_2$ is phenyl, substituted phenyl or substituted alkyl;
wherein $R_1$ and $R_2$ may be joined to form a conjugated ring system which is optionally substituted, which is present in the substrate, is deprotected by acid to form the corresponding ketone photoinitiator species, and
exposing the substrate to electromagnetic radiation of a wavelength or energy which is suitable to generate a reactive species from the deprotected ketone photoinitiator species, the reactive species either directly or indirectly causing transformation of the reactive substrate.

2. A method according to claim 1, wherein the reactive substrate is a coating on a surface of a support.

3. A method according to claim 2, wherein the deprotection of the protected ketone photoinitiator is effected in selected regions of the surface.

4. A method according to claim 2, wherein deprotection is effected throughout the whole surface, and the subsequent photoinitiated reaction is carried out by exposing only portions of the reactive substrate to photoreaction conditions.

5. A method according to claim 1, wherein the substrate further includes a species capable of forming acid in response to an external stimulus, and wherein deprotection of the protected ketone photoinitiator is effected by reaction with acid generated in situ by the said acid forming species in response to exposure of the substrate to an external stimulus.

6. A method according to claim 1, wherein a suitable acid is applied directly to the substrate to deprotect the protected ketone photoinitiator.

7. A method according to claim 1, wherein at least one reactive substrate is selected from the group consisting of: a substrate comprising polymerisable constituents, a substrate comprising cross-linkable constituents, and a substrate comprising colour-changeable constituents.

8. The method according to claim 1, wherein the protected ketone photoinitiator species present in the substrate is deprotected under anhydrous conditions.

9. The method according to claim 8, wherein the reactive substrate is a coating on a surface of a support.

10. A method according to claim 9, wherein the deprotection of the protected ketone photoinitiator is effected in selected regions of the surface.

11. A method according to claim 9, wherein deprotection is effected throughout the whole surface, and the subsequent photoinitiated reaction is carried out by exposing only portions of the reactive substrate to photoreaction conditions.

12. The method according to claim 8, wherein the substrate further includes a species capable of forming acid in response to an external stimulus, and wherein deprotection of the protected ketone photoinitiator is effected by reaction with acid generated in situ by the said acid forming species in response to exposure of the substrate to an external stimulus.

13. A method according to claim 8, wherein at least one reactive substrate is selected from the group consisting of: a substrate comprising polymerisable constituents, a substrate comprising cross-linkable constituents, and a substrate comprising colour-changeable constituents.

14. The method of claim 1, wherein the protected ketone photoinitiator $R_1$ and $R_2$ is phenyl or substituted phenyl and the respective phenyl groups are liked by a bridging moiety to form a structure having the following framework:

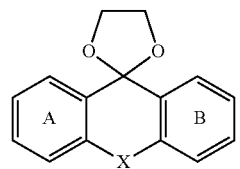

where X is S or >C=O and where each of the A and B rings may be substituted.

15. The method of claim 1, wherein the protected ketone photoinitiator has the formula:

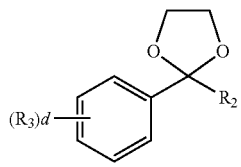

where d is 1 to 5 and where each $R_3$ is independently hydrogen or a substituent selected from alkyl, aryl, alkylthio, aryl thio, or heterocycle; and $R_2$ is phenyl or substituted phenyl or substituted alkyl.

16. The method of claim 15, wherein alkyl is C1-4 alkyl, aryl is phenyl or substituted phenyl, alkylthio is C1-4 alkylthio, aryl thio comprises aryl where aryl is phenyl or substituted phenyl, or heterocycle is morpholino.

17. The method of claim 16, wherein substituted phenyl in each instance is substituted with C1-4 alkyl.

18. A method for the photoinitiated transformation of a transformable reactive substrate, said method comprising:
(a) applying to the surface of a support a coating of the reactive substrate, the substrate being further provided with a protected ketone photoinitiator having the formula:

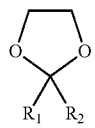

wherein $R_1$ is phenyl or substituted phenyl; $R_2$ is phenyl, substituted phenyl or substituted alkyl;
wherein $R_1$ and $R_2$ may be joined to form a conjugated ring system which is optionally substituted, and one or more species capable of forming acid in response to an external stimulus,
(b) applying an external stimulus to said coating to form acid where the external stimulus is applied, whereby said acid reacts with and causes deprotection of the protected ketone photoinitiator, and wherein the external stimulus is not effective to generate reactive species from the deprotected ketone photoinitiator; and
(c) exposing the coating to electromagnetic radiation of a suitable wavelength or energy to generate a reactive species from the ketone photoinitiator which, directly or indirectly, causes transformation of the transformable reactive substrate in said regions.

19. A method according to claim 18, wherein the deprotection of the protected ketone photoinitiator is effected in selected regions of the surface.

20. A method according to claim 18, wherein deprotection is effected throughout the whole surface, and the subsequent photoinitiated reaction is carried out by exposing only portions of the reactive substrate to photoreaction conditions.

21. A method for the photoinitiated transformation of a transformable reactive substrate, said method comprising:
(a) applying to the surface of a support a coating which comprises the reactive substrate and a protected ketone photoinitiator, having the formula:

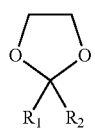

wherein $R_1$ is phenyl or substituted phenyl; $R_2$ is phenyl, substituted phenyl or substituted alkyl,
wherein $R_1$ and $R_2$ may be joined to form a conjugated ring system which is optionally substituted,
(b) applying an acid to said coating to cause deprotection of the protected ketone photoinitiator; and
(c) exposing the coating to electromagnetic radiation of a suitable wavelength or energy to generate a reactive species from the ketone photoinitiator which, directly or indirectly, causes transformation of the transformable reactive substrate in said regions.

22. A method for a photoinitiated transformation of a reactive substrate which makes use of a ketone photoinitiator in at least one stage of the method, the method comprising forming the ketone photoinitiator in situ by deprotection with acid of a protected form of the ketone photoinitiator having the formula:

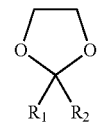

wherein $R_1$ is phenyl or substituted phenyl; $R_2$ is phenyl, substituted Phenyl or substituted alkyl;
wherein $R_1$ and $R_2$ may be joined to form a conjugated ring system which is optionally substituted.

23. A method for the photoinitiated transformation of a transformable reactive substrate, said method comprising:
(a) applying to the surface of a support a coating of the reactive substrate, the substrate being further provided with a protected ketone photoinitiator having the formula:

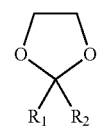

wherein $R_1$ is phenyl or substituted phenyl; $R_2$ is phenyl, substituted phenyl or substituted alkyl;
wherein $R_1$ and $R_2$ may be joined to form a conjugated ring system which is optionally substituted, and one or more species capable of forming acid in response to an external stimulus,
(b) applying an external stimulus to said coating to form acid where the external stimulus is applied, whereby said acid reacts with and causes deprotection of the protected ketone photoinitiator under anhydrous conditions, and wherein the external stimulus is not effective to generate reactive species from the deprotected ketone photoinitiator; and
(c) exposing the coating to electromagnetic radiation of a suitable wavelength or energy to generate a reactive species from the ketone photoinitiator which, directly or indirectly, causes transformation of the transformable reactive substrate in said regions.

* * * * *

UNITED STATES PATENT AND TRADEMARK OFFICE
CERTIFICATE OF CORRECTION

PATENT NO. : 10,221,193 B2  
APPLICATION NO. : 13/522812  
DATED : March 5, 2019  
INVENTOR(S) : Robert A. W. Johnstone and Rui Manuel da Silva Loureiro Page 1 of 1

It is certified that error appears in the above-identified patent and that said Letters Patent is hereby corrected as shown below:

On the Title Page

(73) Assignee, please replace the name of the Assignee "Lintfiled Limited" with --Lintfield Limited--

Signed and Sealed this  
Twenty-second Day of October, 2019

Andrei Iancu  
*Director of the United States Patent and Trademark Office*